United States Patent
Mooney et al.

(10) Patent No.: US 12,090,069 B2
(45) Date of Patent: Sep. 17, 2024

(54) SYSTEMS AND METHODS FOR A WATER RESISTANT ACTIVE EXOSKELETON

(71) Applicant: Dephy, Inc., Maynard, MA (US)

(72) Inventors: Luke Mooney, Sudbury, MA (US); Jonathan Cummings, Concord, MA (US); Jean-François Duval, Belmont, MA (US)

(73) Assignee: Dephy, Inc.

( * ) Notice: Subject to any disclaimer, the term of this patent is extended or adjusted under 35 U.S.C. 154(b) by 1007 days.

(21) Appl. No.: 17/002,556

(22) Filed: Aug. 25, 2020

(65) Prior Publication Data
US 2022/0066513 A1   Mar. 3, 2022

(51) Int. Cl.
| | | |
|---|---|---|
| *A61F 2/66* | (2006.01) | |
| *A61F 5/01* | (2006.01) | |
| *A61H 3/00* | (2006.01) | |
| *B25J 9/00* | (2006.01) | |
| *G06F 1/16* | (2006.01) | |

(52) U.S. Cl.
CPC .......... *A61F 2/6607* (2013.01); *A61F 5/0102* (2013.01); *A61H 3/00* (2013.01); *B25J 9/0006* (2013.01); *A61F 2005/0155* (2013.01); *G06F 1/1656* (2013.01)

(58) Field of Classification Search
CPC .................. A61F 2/6607; A61F 5/0102; A61F 2005/0155; B25J 9/0006; G06F 1/1656; A61H 3/00; A61H 2003/007
USPC .......................................................... 602/27
See application file for complete search history.

(56) References Cited

U.S. PATENT DOCUMENTS

| | | | |
|---|---|---|---|
| 2,477,591 | A | 8/1949 | Follis |
| 2,516,872 | A | 8/1950 | Hauser et al. |
| 2,573,698 | A | 11/1951 | Ellery |
| 3,064,644 | A | 11/1962 | Patterson |

(Continued)

FOREIGN PATENT DOCUMENTS

| | | |
|---|---|---|
| CA | 2937610 A1 | 7/2009 |
| CN | 202679044 U | 1/2013 |

(Continued)

OTHER PUBLICATIONS

US Non-Final Office Action on U.S. Appl. No. 17/867,162 dated Apr. 12, 2023 (32 pages).

(Continued)

*Primary Examiner* — Keri J Nelson
*Assistant Examiner* — Seth R. Brown
(74) *Attorney, Agent, or Firm* — Foley & Lardner LLP

(57) ABSTRACT

An apparatus for a water resistant active exoskeleton boot includes a shin pad and one or more housings. The one or more housings enclose electronic circuitry and an electric motor that generate torque about an axis of rotation of an ankle joint of the user. A sealant is placed in contact with the one or more housings to close the one or more housings and prevent an ingress of water into the one or more housings. The apparatus includes an output shaft coupled to the electric motor and extending through a bore in a housing of the one or more housings enclosing the electric motor. The apparatus includes a seal to prevent an ingress of the water into the one or more housings. The apparatus includes a rotary encoder enclosed within the one or more housings to measure an angle of the electric motor.

20 Claims, 20 Drawing Sheets

(56) References Cited

U.S. PATENT DOCUMENTS

| | | | |
|---|---|---|---|
| 5,490,831 A | 2/1996 | Myers et al. | |
| 5,685,830 A | 11/1997 | Bonutti | |
| 6,299,588 B1 | 10/2001 | Fratrick | |
| 6,872,187 B1 | 3/2005 | Stark et al. | |
| 7,153,242 B2 | 12/2006 | Goffer | |
| 7,431,737 B2 | 10/2008 | Ragnarsdottir et al. | |
| 7,531,006 B2 | 5/2009 | Clausen et al. | |
| 7,628,766 B1 | 12/2009 | Kazerooni et al. | |
| 7,811,333 B2 | 10/2010 | Jonsson et al. | |
| 8,114,168 B2 * | 2/2012 | Olafsson | F16C 23/04 |
| | | | 188/297 |
| 8,435,309 B2 | 5/2013 | Gilbert et al. | |
| 8,516,918 B2 | 8/2013 | Jacobsen et al. | |
| 8,585,620 B2 | 11/2013 | McBean et al. | |
| 8,597,369 B2 | 12/2013 | Hansen et al. | |
| 8,734,528 B2 | 5/2014 | Herr et al. | |
| 8,764,850 B2 | 7/2014 | Hansen et al. | |
| 8,784,350 B2 | 7/2014 | Cohen | |
| 8,790,282 B2 | 7/2014 | Jung et al. | |
| 8,801,802 B2 | 8/2014 | Oddsson et al. | |
| 8,864,846 B2 | 10/2014 | Herr et al. | |
| 8,870,801 B2 | 10/2014 | Tomiyama et al. | |
| 8,870,967 B2 | 10/2014 | Herr et al. | |
| 9,017,419 B1 | 4/2015 | Landry et al. | |
| 9,066,819 B2 | 6/2015 | Gramnaes | |
| 9,078,774 B2 | 7/2015 | Jonsson et al. | |
| 9,198,821 B2 | 12/2015 | Unluhisarcikli et al. | |
| 9,333,097 B2 | 5/2016 | Herr et al. | |
| 9,339,397 B2 | 5/2016 | Herr et al. | |
| 9,345,608 B2 | 5/2016 | Phillips | |
| 9,351,900 B2 | 5/2016 | Walsh et al. | |
| 9,480,618 B2 | 11/2016 | Hsiao-Wecksler et al. | |
| 9,539,117 B2 | 1/2017 | Herr et al. | |
| 9,554,922 B2 | 1/2017 | Casler et al. | |
| 9,662,262 B2 | 5/2017 | Hollander et al. | |
| 9,693,883 B2 | 7/2017 | Herr et al. | |
| 9,707,104 B2 | 7/2017 | Clausen | |
| 9,737,419 B2 | 8/2017 | Herr et al. | |
| 9,808,390 B2 | 11/2017 | Caires et al. | |
| 9,839,552 B2 | 12/2017 | Han et al. | |
| 9,872,782 B2 | 1/2018 | Herr et al. | |
| 9,907,722 B2 | 3/2018 | Aguirre-Ollinger et al. | |
| 9,925,071 B2 | 3/2018 | Langlois et al. | |
| 9,980,873 B2 | 5/2018 | Tung et al. | |
| 10,195,057 B2 | 2/2019 | Clausen | |
| 10,251,762 B2 | 4/2019 | Langlois | |
| 10,307,271 B2 | 6/2019 | Holgate et al. | |
| 10,307,272 B2 | 6/2019 | Herr et al. | |
| 10,335,294 B2 | 7/2019 | Huang et al. | |
| 10,369,023 B2 | 8/2019 | Simon et al. | |
| 10,405,996 B2 | 9/2019 | Langlois | |
| 10,406,002 B2 | 9/2019 | Herr et al. | |
| 10,426,637 B2 | 10/2019 | Tong et al. | |
| 10,463,561 B2 | 11/2019 | Zhang et al. | |
| 10,485,681 B2 | 11/2019 | Herr et al. | |
| 10,532,000 B1 | 1/2020 | De Sapio et al. | |
| 10,537,449 B2 | 1/2020 | Han et al. | |
| 10,561,563 B2 | 2/2020 | Herr et al. | |
| 10,576,620 B1 | 3/2020 | Chou et al. | |
| 11,413,210 B2 * | 8/2022 | Contreras-Vidal | A61F 5/0123 |
| 2006/0167564 A1 | 7/2006 | Flaherty et al. | |
| 2006/0184280 A1 | 8/2006 | Oddsson et al. | |
| 2007/0225620 A1 | 9/2007 | Carignan et al. | |
| 2009/0030530 A1 | 1/2009 | Martin | |
| 2009/0210093 A1 | 8/2009 | Jacobsen et al. | |
| 2009/0222105 A1 | 9/2009 | Clausen et al. | |
| 2010/0198124 A1 | 8/2010 | Bhugra | |
| 2010/0231206 A1 * | 9/2010 | Kobayashi | G01B 7/30 |
| | | | 324/207.25 |
| 2011/0066088 A1 | 3/2011 | Little et al. | |
| 2012/0089063 A1 | 4/2012 | Olson et al. | |
| 2012/0256381 A1 | 10/2012 | Bradshaw | |
| 2012/0289870 A1 * | 11/2012 | Hsiao-Wecksler | A61H 3/00 |
| | | | 601/5 |
| 2013/0090580 A1 | 4/2013 | Hong et al. | |
| 2013/0226048 A1 * | 8/2013 | Unluhisarcikli | A61H 1/0244 |
| | | | 601/34 |
| 2013/0231595 A1 | 9/2013 | Zoss et al. | |
| 2014/0100494 A1 | 4/2014 | Sarkodie-Gyan et al. | |
| 2014/0330431 A1 | 11/2014 | Hollander et al. | |
| 2015/0141878 A1 | 5/2015 | Roy et al. | |
| 2015/0164731 A1 | 6/2015 | Kwak et al. | |
| 2015/0173993 A1 | 6/2015 | Walsh et al. | |
| 2015/0196403 A1 | 7/2015 | Kim et al. | |
| 2015/0257902 A1 | 9/2015 | Martin | |
| 2016/0107309 A1 | 4/2016 | Walsh et al. | |
| 2016/0143800 A1 | 5/2016 | Hyung et al. | |
| 2016/0278948 A1 | 9/2016 | Piercy et al. | |
| 2016/0331557 A1 | 11/2016 | Tong et al. | |
| 2016/0331624 A1 | 11/2016 | Sankai et al. | |
| 2017/0043482 A1 | 2/2017 | Hyun et al. | |
| 2017/0119132 A1 | 5/2017 | Pruess et al. | |
| 2017/0202724 A1 | 7/2017 | De Rossi et al. | |
| 2017/0354529 A1 | 12/2017 | Han et al. | |
| 2018/0104075 A1 * | 4/2018 | Mooney | A61H 1/024 |
| 2018/0116826 A1 | 5/2018 | Byars et al. | |
| 2018/0125738 A1 | 5/2018 | Witte et al. | |
| 2018/0177665 A1 | 6/2018 | Rogozinski | |
| 2018/0193172 A1 | 7/2018 | Smith et al. | |
| 2018/0200135 A1 | 7/2018 | Tung et al. | |
| 2018/0325764 A1 | 11/2018 | Yagi | |
| 2019/0011743 A1 | 1/2019 | Yan et al. | |
| 2019/0038448 A1 | 2/2019 | Choi et al. | |
| 2019/0065970 A1 | 2/2019 | Bonutti et al. | |
| 2019/0070060 A1 | 3/2019 | Choi et al. | |
| 2019/0083002 A1 | 3/2019 | Jang et al. | |
| 2019/0105215 A1 | 4/2019 | Dalley et al. | |
| 2019/0125004 A1 | 5/2019 | Thomas et al. | |
| 2019/0159728 A1 | 5/2019 | Pritchard et al. | |
| 2019/0159954 A1 | 5/2019 | Ozsecen et al. | |
| 2019/0160321 A1 | 5/2019 | Ozsecen et al. | |
| 2019/0175365 A1 | 6/2019 | Herr et al. | |
| 2019/0183713 A1 | 6/2019 | Sankai | |
| 2019/0254908 A1 | 8/2019 | Ortlieb et al. | |
| 2019/0254909 A1 | 8/2019 | Lee et al. | |
| 2019/0282429 A1 | 9/2019 | Son et al. | |
| 2019/0314185 A1 | 10/2019 | Yuge et al. | |
| 2019/0328552 A1 | 10/2019 | Herr et al. | |
| 2019/0328604 A1 | 10/2019 | Contreras-Vidal et al. | |
| 2019/0343707 A1 | 11/2019 | Riener et al. | |
| 2019/0343710 A1 * | 11/2019 | Lerner | A61H 3/00 |
| 2019/0344433 A1 | 11/2019 | Lerner | |
| 2019/0365554 A1 * | 12/2019 | Davies-Sekle | A61H 1/0281 |
| 2020/0011406 A1 | 1/2020 | Julin | |
| 2020/0016020 A1 | 1/2020 | Mooney et al. | |
| 2020/0018589 A1 * | 1/2020 | Ausserlechner | G01B 7/30 |
| 2020/0085666 A1 | 3/2020 | Seo et al. | |
| 2020/0093679 A1 | 3/2020 | Sonar et al. | |
| 2020/0197253 A1 | 6/2020 | Park et al. | |
| 2020/0253772 A1 * | 8/2020 | Reid | A61F 5/0111 |
| 2020/0253774 A1 | 8/2020 | Pismennaya et al. | |
| 2020/0276698 A1 | 9/2020 | Ding et al. | |
| 2020/0326780 A1 | 10/2020 | Kearney et al. | |
| 2021/0085554 A1 | 3/2021 | Roh et al. | |
| 2021/0121355 A1 | 4/2021 | Behboodi et al. | |
| 2021/0290470 A1 | 9/2021 | Farris et al. | |
| 2021/0291355 A1 | 9/2021 | Lerner et al. | |
| 2021/0369536 A1 | 12/2021 | Mooney et al. | |
| 2021/0393467 A1 | 12/2021 | Ookoba | |
| 2022/0031552 A1 | 2/2022 | Mooney et al. | |
| 2022/0110814 A1 | 4/2022 | Mooney et al. | |
| 2022/0273469 A1 | 9/2022 | Kazerooni et al. | |

FOREIGN PATENT DOCUMENTS

| | | |
|---|---|---|
| CN | 105213155 A | 1/2016 |
| CN | 103813772 B | 7/2016 |
| CN | 104644381 B | 8/2016 |
| CN | 104983543 B | 8/2016 |
| CN | 107115191 A | 9/2017 |
| CN | 107874984 A | 4/2018 |
| CN | 105213153 B | 6/2018 |
| CN | 105963100 B | 7/2018 |
| CN | 108283564 A | 7/2018 |

(56) References Cited

FOREIGN PATENT DOCUMENTS

| | | |
|---|---|---|
| CN | 108338896 A | 7/2018 |
| CN | 108451748 A | 8/2018 |
| CN | 106491319 B | 12/2018 |
| CN | 105456004 B | 2/2019 |
| CN | 109646245 A | 4/2019 |
| CN | 209107991 U | 7/2019 |
| CN | 209270231 | 8/2019 |
| CN | 110327189 A | 10/2019 |
| CN | 110478191 A | 11/2019 |
| CN | 110575350 A | 12/2019 |
| EP | 2 621 413 B1 | 6/2014 |
| EP | 2 564 817 B1 | 1/2019 |
| IN | 201631013395 A | 10/2017 |
| JP | 5935177 B2 | 6/2016 |
| KR | 20140107029 A | 9/2014 |
| WO | WO-2016/180073 A1 | 11/2016 |
| WO | WO-2016/182473 A1 | 11/2016 |
| WO | WO-2018/023109 A1 | 2/2018 |
| WO | WO-2019/060791 A1 | 3/2019 |
| WO | WO-2019/160532 | 8/2019 |

OTHER PUBLICATIONS

Haque et al., Design and Preliminary Testing of an Insrumented Exoskeleton for Walking Gait Measurement, 2019, IEEE, 2019, 6 pages.
International Preliminary Report on Patentability on PCT Appl. Ser. No. PCT/US2021/047252 dated Mar. 9, 2023 (9 pages).
International Preliminary Report on Patentability on PCT Appl. Ser. No. PCT/US2020/059866 dated May 27, 2022 (14 pages).
International Preliminary Report on Patentability on PCT Appl. Ser. No. PCT/US2021/034086 dated Dec. 15, 2022 (10 pages).
International Preliminary Report on Patentability on PCT Appl. Ser. No. PCT/US2021/034163 dated Dec. 15, 2022 (6 pages).
International Preliminary Report on Patentability on PCT Appl. Ser. No. PCT/US2021/034182 dated Dec. 15, 2022 (5 pages).
International Preliminary Report on Patentability on PCT Appl. Ser. No. PCT/US2021/034252 dated Dec. 15, 2022 (14 pages).
International Search Report and the Written Opinion on PCT Appl. Ser. No. PCT/US2021/034086 dated Jun. 28, 2021 (11 pages).
International Search Report and the Written Opinion on PCT Appl. Ser. No. PCT/US2021/034163 dated Jun. 25, 2021 (7 pages).
International Search Report and the Written Opinion on PCT Appl. Ser. No. PCT/US2021/034182 dated Jun. 29, 2021 (6 pages).
International Search Report and the Written Opinion on PCT Appl. Ser. No. PCT/US2021/034252 dated Jun. 28, 2021 (15 pages).
International Search Report and the Written Opinion on PCT Appl. Ser. No. PCT/US2021/047252 dated Nov. 23, 2021 (10 pages).
International Search Report and the Written Opinion on PCT Appl. Ser. No. PCT/US2021/047295 dated Sep. 23, 2021 (7 pages).
Pirjade et al., "Design and Fabrication of a Low-cost Human Body Lower Limb Exoskeleton," IEEE, Apr. 16, 2020, pp. 32-37.
Sanz-Morere et al., "A Knee-Ankle-Foot Orthosis to Assist the Sound Limb of Transfemoral Amputees," IEEE, vol. 1, No. 1, Feb. 13, 2019, pp. 38-48.
US Final Office Action on U.S. Appl. No. 17/028,761 dated Mar. 16, 2021 (18 pages).
US Final Office Action on U.S. Appl. No. 17/136,333 dated Jun. 21, 2021 (27 pages).
US Non-Final Office Action on U.S. Appl. No. 17/022,982 dated May 4, 2021 (19 pages).
US Non-Final Office Action on U.S. Appl. No. 17/028,761 dated Nov. 23, 2020 (18 pages).
US Non-Final Office Action on U.S. Appl. No. 17/028,761 dated Oct. 12, 2021 (24 pages).
US Non-Final Office Action on U.S. Appl. No. 17/136,333 dated Mar. 12, 2021 (24 pages).
US Non-Final Office Action on U.S. Appl. No. 17/136,333 dated Nov. 23, 2021 (28 pages).
US Non-Final Office Action on U.S. Appl. No. 17/504,261 dated Dec. 20, 2022 (9 pages).
US Non-Final Office Action on U.S. Appl. No. 17/526,454 dated Jan. 12, 2023 (22 pages).
US Notice of Allowance on U.S. Appl. No. 17/022,982 dated Jan. 29, 2021 (12 pages).
US Notice of Allowance on U.S. Appl. No. 17/022,982 dated Sep. 27, 2021 (9 pages).
US Notice of Allowance on U.S. Appl. No. 17/028,761 dated Feb. 2, 2022 (10 pages).
US Notice of Allowance on U.S. Appl. No. 17/084,111 dated Feb. 19, 2021 (13 pages).
US Notice of Allowance on U.S. Appl. No. 17/084,111 dated May 20, 2021 (8 pages).
US Notice of Allowance on U.S. Appl. No. 17/084,111 dated Sep. 16, 2021 (7 pages).
US Notice of Allowance on U.S. Appl. No. 17/109,911 dated Feb. 3, 2021 (10 pages).
US Notice of Allowance on U.S. Appl. No. 17/109,911 dated May 25, 2021 (5 pages).
US Notice of Allowance on U.S. Appl. No. 17/109,911 dated Sep. 14, 2021 (5 pages).
US Notice of Allowance on U.S. Appl. No. 17/136,333 dated Apr. 6, 2022 (13 pages).
Witte et al., "Design of Two Lightweight, High-Bandwidth Torque-Controlled Ankle Exoskeletons," IEEE International Conference on Robotics and Automation (ICRA), May 26, 2015 (6 pages).
Xie et al., "An Unpowered Flexible Lower Limb Exoskeleton: Walking Assisting and Energy Harvesting," IEEE, vol. 24, No. 5, Oct. 5, 2019, pp. 2236-2247.
Zhang et al., "Experimental comparison of torque control methods on an ankle exoskeleton during human walking," IEEE International Conference on Robotics and Automation (ICRA), May 26, 2015 (6 pages).
Zhou et al., "Preliminary Evaluation of Gait Assistance During Treadmill Walking with a Light-weight Bionic Knee Exoskeleton," IEEE, Dec. 7, 2016, pp. 1173-1178.
US Corrected Notice of Allowance on U.S. Appl. No. 17/504,261 dated Apr. 24, 2023 (2 pages).
US Notice of Allowance on U.S. Appl. No. 17/526,454 dated Apr. 26, 2023 (8 pages).
International Preliminary Report on Patentability on PCT Appl. Ser. No. PCT/US2021/047295 dated Mar. 30, 2023 (5 pages).
US Final Office Action on U.S. Appl. No. 17/526,454 dated Apr. 7, 2023 (6 pages).
US Notice of Allowance on U.S. Appl. No. 17/504,261 dated Apr. 7, 2023 (9 pages).
EP Office Action on EP Appl. Ser. No. 20888375.1 dated Sep. 14, 2023 (7 pages).
US Corrected Notice of Allowance on U.S. Appl. No. 17/504,261 dated May 18, 2023 (2 pages).
US Non-Final Office Action on U.S. Appl. No. 17/504,248 dated Jun. 7, 2023 (12 pages).
US Notice of Allowance on U.S. Appl. No. 17/867,162 dated Aug. 30, 2023 (17 pages).
US Notice of Allowance on U.S. Appl. No. 17/867,162 dated Oct. 5, 2023 (18 pages).
Dollar et al., Active Orthoses for the Lower-Limbs: Challenges and State of the Art, 2008, IEEE, p. 968-977 (Year: 2008).
Dollar et al., Lower Extremity Exoskeletons and Active Orthoses: Challenges and State-of-the-Art, 2008, IEEE, p. 144-158 (Year:2008).
Goldfarb et al. Design of a Controlled-Brake Orthosis for FES-aided gait, 1996, IEEE, p. 13-24 (Year:1996).
International Search Report and Written Opinion on PCT/US2020/059866 dated Feb. 4, 2021, 8 pages.
Kim et al., Mechanical Design of the Hanyang Exoskeleton Assistive Robot (HEXAR), 2014, IEEE, 479-484 (Year: 2014).
European Extended Search Report issued in corresponding European Patent Application No. 21818627.8 dated May 15, 2024.
European Extended Search Report issued in corresponding European Patent Application No. 21817832.5 dated May 29, 2024 (10 pages).

(56) References Cited

OTHER PUBLICATIONS

Partial Supplementary European Search Report issued in corresponding European Patent Application No. 21817291.4 dated May 23, 2024 (11 pages).
US Non-Final Office Action on U.S. Appl. No. 18/238,612 dated Jun. 3, 2024.
European Extended Search Report issued in corresponding European Patent Application No. 21817826.7 dated Jun. 14, 2024 (6 pages).

* cited by examiner

SYSTEMS AND METHODS FOR A WATER RESISTANT ACTIVE EXOSKELETON

GOVERNMENT RIGHTS

This invention was made with government support under contract no. W911QY-19-9-0007 awarded by Natick Contracting Division. This Agreement is not subject to the Bayh-Dole Act, 35 U.S.C. §§ 200-212.

TECHNICAL FIELD

The present disclosure generally relates to the field of exoskeletons.

BACKGROUND

Exoskeletons can be worn by a user to facilitate movement of limbs of the user.

SUMMARY

At least one aspect of the present disclosure is directed to an apparatus for a water resistant active exoskeleton boot. The apparatus can include a shin pad to be coupled to a shin of a user and at least one housing of one or more housings. The one or more housings can enclose electronic circuitry and an electric motor that can generate torque about an axis of rotation of an ankle joint of the user. A sealant can be placed in contact with the one or more housings to close the one or more housings and prevent an ingress of water into the one or more housings. The apparatus can include an output shaft coupled to the electric motor and extending through a bore in a housing of the one or more housings enclosing the electric motor. The apparatus can include a seal in contact with the output shaft and a portion of the housing including the bore. The seal can prevent an ingress of the water into the one or more housings. The apparatus can include a rotary encoder enclosed within the one or more housings to measure an angle of the electric motor. The electronic circuitry can receive, from the rotary encoder, an indication of the angle of the electric motor and can control, based on the indication of the angle of the electric motor, operation of the electric motor to generate torque about the axis of rotation of the ankle joint of the user.

Another aspect of the present disclosure is directed to a method of augmenting user motion. The method can include providing, to a user, a water resistant active exoskeleton boot. The water resistant active exoskeleton boot can include a shin pad to be coupled to a shin of a user and at least one housing of one or more housings. The one or more housings can enclose electronic circuitry and an electric motor that can generate torque about an axis of rotation of an ankle joint of the user. A sealant can be placed in contact with the one or more housings to close the one or more housings and prevent an ingress of water into the one or more housings. The water resistant active exoskeleton boot can include an output shaft coupled to the electric motor and extending through a bore in a housing of the one or more housings enclosing the electric motor. The water resistant active exoskeleton boot can include a seal in contact with the output shaft and a portion of the housing comprising the bore, the seal to prevent an ingress of the water into the one or more housings. The water resistant active exoskeleton boot can include a rotary encoder enclosed within the one or more housings to measure an angle of the electric motor. The electronic circuitry can receive, from the rotary encoder, an indication of the angle of the electric motor and can control, based on the indication of the angle of the electric motor, operation of the electric motor to generate torque about the axis of rotation of the ankle joint of the user.

Those skilled in the art will appreciate that the summary is illustrative only and is not intended to be in any way limiting. Other aspects, inventive features, and advantages of the devices and/or processes described herein, as defined solely by the claims, will become apparent in the detailed description set forth herein and taken in conjunction with the accompanying drawings.

BRIEF DESCRIPTION OF THE DRAWINGS

The details of one or more implementations of the subject matter described in this specification are set forth in the accompanying drawings and the description below. Other features, aspects, and advantages of the subject matter will become apparent from the description, the drawings, and the claims.

Like reference numbers and designations in the various drawings indicate like elements.

DETAILED DESCRIPTION

This disclosure relates generally to performance enhancing wearable technologies. Particularly, this disclosure relates to apparatuses, systems, and methods for water resistant active exoskeletons (e.g., waterproof active exoskeletons). The exoskeleton can operate in an environment in which the exoskeleton is wetted or submerged in water. The exoskeleton can have an onboard power source that is used to power electronics and one or more actuators.

I. Exoskeleton Overview

Exoskeletons (e.g., lower limb exoskeleton, knee exoskeleton, or back exoskeleton) can include devices worn by a person to augment physical abilities. Exoskeletons can be considered passive (e.g., not requiring an energy source such as a battery) or active (e.g., requiring an energy source to power electronics and usually one or many actuators). Exoskeletons may be capable of providing large amounts of force, torque and/or power to the human body in order to assist with motion.

Exoskeletons can transfer energy to the user or human. Exoskeletons may not interfere with the natural range of motion of the body. For example, exoskeletons can allow a user to perform actions (e.g., walking, running, reaching, or jumping) without hindering or increasing the difficulty of performing these actions. Exoskeletons can reduce the difficulty of performing these actions by reducing the energy or effort the user would otherwise exert to perform these actions. Exoskeletons can convert the energy into useful mechanical force, torque, or power. Onboard electronics (e.g., controllers) can control the exoskeleton. Output force and torque sensors can also be used to make controlling easier.

Figure 1:
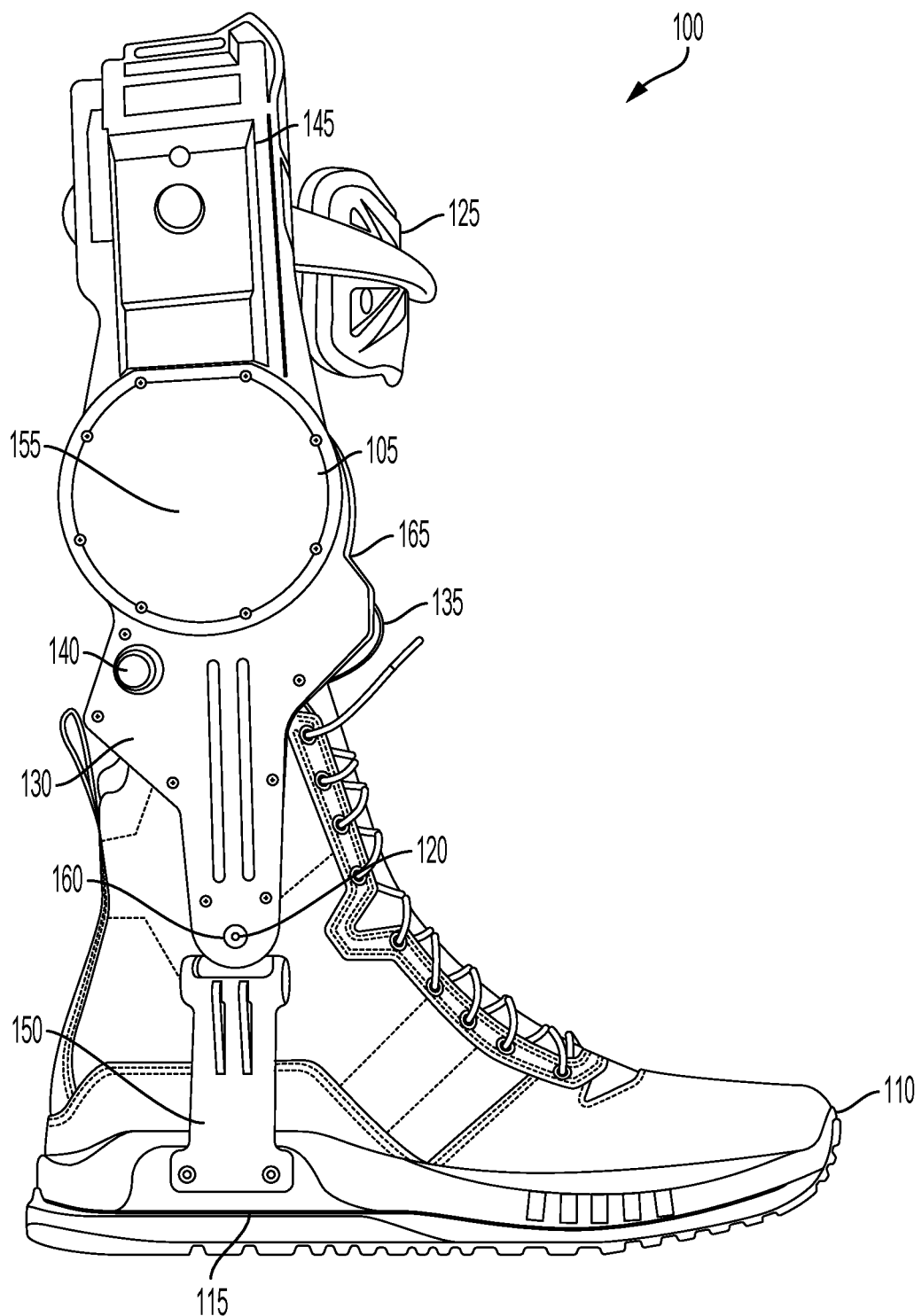
FIG. 1 illustrates a schematic diagram of an exoskeleton, according to an embodiment.

FIG. 1 illustrates a schematic diagram of an exoskeleton 100. The exoskeleton 100 can be referred to as a lower limb exoskeleton, lower limb exoskeleton assembly, lower limb exoskeleton system, ankle exoskeleton, ankle foot orthosis, knee exoskeleton, hip exoskeleton, exoskeleton boot, or exoboot. The exoskeleton 100 can include a water resistant active exoskeleton boot. For example, the exoskeleton 100 can resist the penetration of water into the interior of the exoskeleton 100. The exoskeleton 100 can include a water resistant active exoskeleton boot. For example, the exoskeleton 100 can be impervious to liquids (e.g., water) and non-liquids (e.g., dust, dirt, mud, sand, or debris). The exoskeleton 100 can remain unaffected by water or resist the ingress of water, such as by decreasing a rate of water flow into the interior of the exoskeleton 100 to be less than a target rate indicative of being water resistant or waterproof. For example, the exoskeleton 100 can operate in 3 feet of water for a duration of 60 minutes. The exoskeleton 100 can have an ingress protection rating (IP) rating of 68. The exoskeleton 100 can have a National Electrical Manufacturer Association (NEMA) rating of 4×.

The exoskeleton 100 can include a shin pad 125 (e.g., shin guard). The shin pad 125 can be coupled to a shin of a user and at least one housing of one or more housings 105. The shin pad 125 can be coupled to the at least one housing via a shin lever. The shin lever can extend from the at least one housing to the shin pad 125. The shin lever can include a mechanical structure that connects the shin pad 125 to a chassis. The chassis can include a mechanical structure that connects static components. The shin pad 125 can be coupled to the shin of the user to provide support. The shin pad 125 can include a piece of equipment to protect the user from injury. For example, the shin pad 125 can protect the lower extremities of the user from external impact. The shin pad 125 can interface with the shin of the user. The shin pad 125 can include a band (e.g., adjustable band) configured to wrap around the shin of the user. The shin pad 125 can secure the upper portion of the exoskeleton 100 to the body of the user. The shin pad 125 can secure or help secure the exoskeleton 100 to the shin, leg, or lower limb of the user. The shin pad 125 can provide structural integrity to the exoskeleton 100. The shin pad 125 can support other components of the exoskeleton 100 that can be coupled to the shin pad 125. The shin pad 125 can be made of lightweight, sturdy, and/or water resistant materials. For example, the shin pad 125 can be made of plastics, aluminum, fiberglass, foam rubber, polyurethane, and/or carbon fiber.

The one or more housings 105 can enclose electronic circuitry. The one or more housings 105 can encapsulate all the electronics of the exoskeleton 100. The one or more housings 105 can include an electronics cover (e.g., case). The one or more housings 105 can enclose an electric motor (e.g., motor). The electric motor can generate torque about an axis of rotation of an ankle joint of the user. The ankle joint can allow for dorsiflexion and/or plantarflexion of the user's foot. The exoskeleton 100 can include an ankle joint component 120 that rotates about the axis of rotation the ankle joint. The ankle joint component 120 can be positioned around or adjacent to the ankle joint.

The exoskeleton 100 can include a rotary encoder 155 (e.g., shaft encoder, first rotary encoder, or motor encoder). The rotary encoder 155 can be enclosed within the one or more housings 105. The rotary encoder 155 can measure an angle of the electric motor. The angle of the electric motor can be used by the controller to determine an amount of torque applied by the exoskeleton 100. For example, the angle of the electric motor can correspond to an amount of torque applied by the exoskeleton 100. An absolute angle of the electric motor can correspond to an amount of torque applied by the exoskeleton 100. The rotary encoder 155 can include an inductive encoder. The ankle joint component 120 can be actuated by a motor (e.g., electric motor). The rotary encoder 155 can include a contactless magnetic encoder or an optical encoder.

The exoskeleton 100 can include a second rotary encoder 160 (e.g., ankle encoder). The second rotary encoder 160 can measure an angle of the ankle joint. The angle of the ankle joint can be used by the controller to determine an amount of torque applied by the exoskeleton 100. The second rotary encoder 160 can include a first component enclosed in the one or more housings 105 and in communication with the electronic circuitry. The second rotary encoder 160 can include a second component located outside the one or more housings 105 and configured to interact with the first component. The second rotary encoder 160 can include a contactless magnetic encoder, a contactless inductive encoder, or an optical encoder. The second rotary encoder 160 can detect the angle of the ankle joint while the rotary encoder 155 can detect the angle of the electric motor. The angle of the electric motor can be different from the angle of the ankle joint. The angle of the electric motor can be independent of the angle of the ankle joint. The angle of the ankle joint can be used to determine an output (e.g., torque) of the electric motor. The ankle joint component 120 can be coupled to the second rotary encoder 160.

The one or more housings 105 can encapsulate electronics that are part of the exoskeleton 100. The one or more housings 105 can form a fitted structure (e.g., clamshell structure) to enclose the electronic circuitry and the electric motor. The fitted structure can be formed from two or more individual components. The individual components of the fitted structure can be joined together to form a single unit. The one or more housings 105 can be formed of plastic or metal (e.g., aluminum). An adhesive sealant can be placed between individual components of the fitted structure and under the electronics cover. A gasket can be placed between individual components of the fitted structure and under the electronics cover. The gasket can be placed in the seam between the individual components of the fitted structure.

A sealant 165 can be placed in contact with the one or more housings 105 to close the one or more housings 105 and prevent an ingress of water into the one or more housings 105. The sealant 165 used to close the one or more housings 105 can include an adhesive sealant (e.g., super glue, epoxy resin, or polyvinyl acetate). The adhesive sealant can include a substance used to block the passage of fluids through the surface or joints of the one or more housings 105. The sealant 165 used to close the one or more housings 105 can include epoxy. The sealant 165 can permanently seal or close the one or more housings 105. For example, the sealant 165 can seal or close the one or more housings 105 such that the one or more housings are not removably attached to one another.

The exoskeleton 100 can couple with a boot 110. For example, the exoskeleton 100 can be attached to the boot 110. The boot 110 can be worn by the user. The boot 110 can be connected to the exoskeleton 100. The exoskeleton 100 can be compatible with different boot shapes and sizes.

The exoskeleton 100 can include an actuator 130 (e.g., actuator lever arm, or actuator module). The actuator 130 can include one or more of the components in the exoskeleton 100. For example, the actuator 130 can include the one or more housings 105, the footplate 115, the ankle joint component 120, the actuator belt 135, and the post 150, while excluding the boot 110. The boot 110 can couple the user to the actuator 130. The actuator 130 can provide torque to the ground and the user.

The exoskeleton 100 can include a footplate 115 (e.g., carbon insert, carbon shank). The footplate 115 can include a carbon fiber structure located inside of the sole of the boot 110. The footplate 115 can be made of a carbon-fiber composite. The footplate 115 can be inserted into the sole of the boot 110. The footplate 115 can be used to transmit torque from the actuator 130 to the ground and to the user. The footplate 115 can be located in the sole of the exoskeleton 100. This footplate 115 can have attachment points that allow for the connection of the exoskeleton's mechanical structure. An aluminum insert with tapped holes and cylindrical bosses can be bonded into the footplate 115. This can create a rigid mechanical connection to the largely compliant boot structure. The bosses provide a structure that can be used for alignment. The footplate 115 can be sandwiched between two structures, thereby reducing the stress concentration on the part. This design can allow the boot to function as a normal boot when there is no actuator 130 attached.

The exoskeleton 100 can include an actuator belt 135 (e.g., belt drivetrain). The actuator belt 135 can include a shaft that is driven by the motor and winds the actuator belt 135 around itself. The actuator belt 135 can include a tensile member that is pulled by the spool shaft and applies a force to the ankle lever. Tension in the actuator belt 135 can apply a force to the ankle lever. The exoskeleton 100 can include an ankle lever. The ankle lever can include a lever used to transmit torque to the ankle. The exoskeleton 100 can be used to augment the ankle joint.

The exoskeleton 100 can include a power button 140 (e.g., power switch). The power button 140 can power the electronics of the exoskeleton 100. The power button 140 can be located on the exterior of the exoskeleton 100. The power button 140 can be coupled to the electronics in the interior of the exoskeleton 100. The power button 140 can be electrically connected to an electronic circuit. The power button 140 can include a switch configured to open or close the electronic circuit. The power button 140 can include a low-power, momentary push-button configured to send power to a microcontroller. The microcontroller can control an electronic switch.

The exoskeleton 100 can include a battery 145 (e.g., battery module). The battery 145 can power the exoskeleton 100. The battery 145 can include one or more electrochemical cells. The battery 145 can supply electric power to the exoskeleton 100. The battery 145 can include a power source (e.g., onboard power source). The power source can be used to power electronics and one or more actuators. The battery 145 can include a battery pack. The battery pack can be coupled to the one or more housings 105 below a knee of the user. The battery pack can include an integrated battery pack. The exoskeleton 100 can use waist mount batteries and run cables to transmit power to the exoskeleton 100. The integrated battery pack can remove the need for power cables, which can reduce the snag hazards of the system. The integrated battery pack can allow the system to be a stand-alone unit mounted to the user's lower limb. The battery 145 can include an integrated battery management system to perform various operations. For example, the system can optimize the energy density of the unit, optimize the longevity of the cells, and enforce the required safety to protect the user. The battery 145 can include a removable battery. The battery 145 can be referred to as a local battery because it is located on the exoboot 100 (e.g., on the lower limb or below the knee of the user), as opposed to located on a waist or back of the user. The battery 145 can include a weight-mounted battery, which can refer to the battery being held in place on the exoboots 100 via gravity and friction, as opposed to a latching mechanism. The battery 145 can include a water resistant battery or a waterproof battery. The exoskeleton 100 and the battery 145 can include water resistant connectors.

The exoskeleton 100 can include a post 150. The post 150 can include a mechanical structure that connects to the boot 110. The post 150 can couple the ankle joint component 120 with the footplate 115. The post 150 can be attached at a first end to the footplate 115. The post 150 can be attached at a second end to the ankle joint component 120. The post 150 can pivot about the ankle joint component 120. The post 150 can include a mechanical structure that couples the footplate 115 with the ankle joint component 120. The post 150 can include a rigid structure. The post 150 can be removably attached to the footplate 115. The post 150 can be removably attached to the ankle joint component 120. For example, the post 150 can be disconnected from the ankle joint component 120.

The exoskeleton 100 can include a rugged system used for field testing. The exoskeleton 100 can include an integrated ankle lever guard (e.g., nested lever). The exoskeleton 100 can include a mechanical shield to guard the actuator belt 135 and ankle lever transmission from the environment. The housing structure of the system can extend to outline the range of travel of the ankle lever (e.g., lever arm 1240) on the lateral and medial side.

II. Water Resistant Active Exoskeleton

Using the exoskeleton 100 in environments where the exoskeleton 100 is exposed to water, fluids, dirt, sand, gravel, or debris can negatively impact the performance of the exoskeleton or damage one or more component of the exoskeleton 100. For example, fluids or debris can enter one or more components, such as the electronic circuitry or electric motor, thereby damaging the component. Thus, systems, methods and apparatus of the present technical solution provide a water resistant active exoskeleton that can perform as desired in in environments containing water, mud, sand or other fluids or debris (e.g., outdoors, industrial environments, or fields). By having fewer electrical or mechanical components, or enclosing electrical or mechanical components in a protective, water resistant housing, the water resistant active exoskeleton of this technical solution can perform in various environments with increased reliability and longevity without damage to the components. The simplicity of assembly can reduce donning and/or doffing time and can improve wearability of the exoskeleton. Simplicity of wearing the exoskeleton 100 can be important for users with a wider range of physical and intellectual abilities. The water resistant active exoskeleton can reduce snagging hazards by eliminating exposed cables.

The number of individual components of exoskeleton 100 can be minimized to decrease the number of possible entry points for water or debris to enter the exoskeleton 100. The possible entry points can include seams and/or moving parts of the exoskeleton 100. The seams can be permanently sealed via a sealant. One challenge with waterproofing the exoskeleton 100 is that moisture and water may need to be kept away from the internal electronic components while one or more moving parts interface with the exterior of the exoskeleton 100. The moving parts (e.g., moving surfaces, or rotating parts) can be sealed via the one or more of the seals described herein. For example, the one or more seals can include a precision-machined seal that contacts the moving part. The seal can be designed such that little to no moisture can enter the interior of the exoskeleton 100 while the moving part operates. The one or more seals can include a packing material around the moving part such that the moving part can operate while moisture is kept out of the interior of the exoskeleton 100. The one or more seals can include magnets to transmit torque through a sealing wall. These one or more seals can be used to reduce or prevent water from entering the exoskeleton 100 can interfering or damaging internal electronic components.

Figure 2:
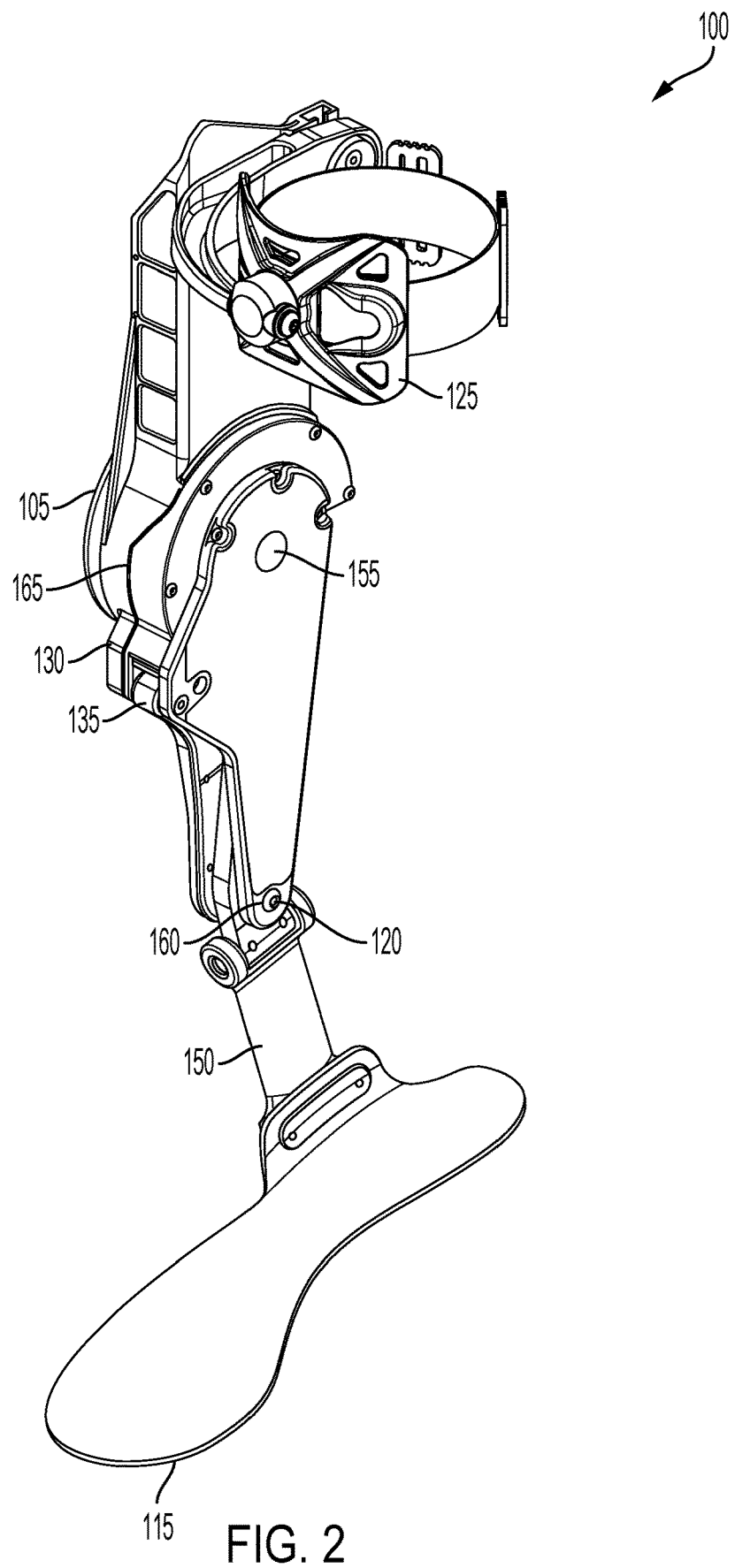
FIG. 2 illustrates a schematic diagram of an exoskeleton, according to an embodiment.
Figure 3:
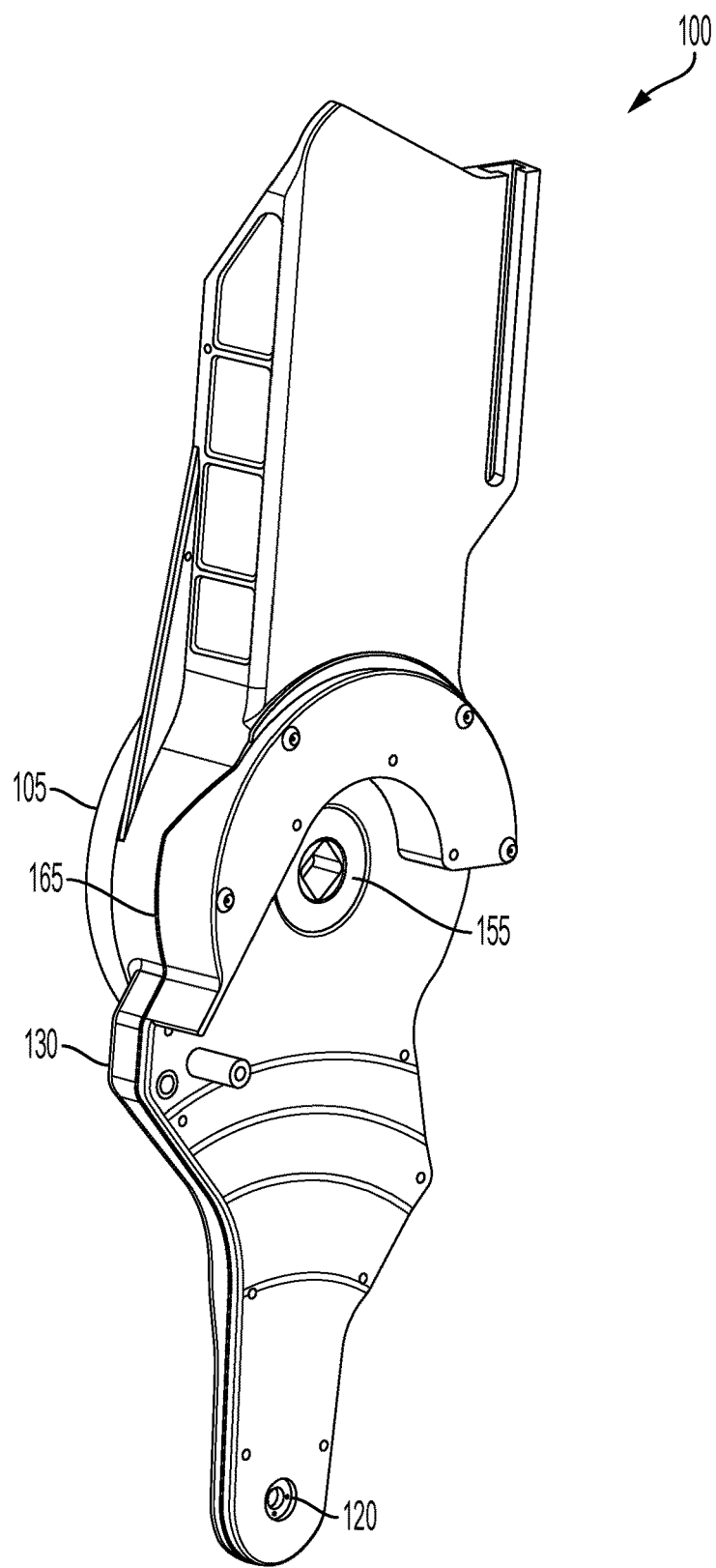
FIG. 3 illustrates a schematic diagram of an exoskeleton, according to an embodiment.

FIG. 2 and FIG. 3 illustrate schematic diagrams of the exoskeleton 100. The exoskeleton 100 can include the one or more housings 105, the footplate 115, the ankle joint component 120, shin pad 125, the actuator 130, the actuator belt 135, the post 150, the rotary encoder 155, the second rotary encoder 160, and the sealant 165 as described above. The one or more housings 105 can be coupled to the shin pad 125. The post 150 can couple the ankle joint component 120 with the footplate 115. The actuator 130 can include the one or more housings 105, the footplate 115, the ankle joint component 120, the actuator belt 135, and the post 150. The rotary encoder 155 can measure an angle of the electric motor. The second rotary encoder 160 can measure an angle of the ankle joint. The sealant 165 can be placed in contact with the one or more housings 105 to close the one or more housings 105 and prevent an ingress of water into the one or more housings 105.

Figure 4:
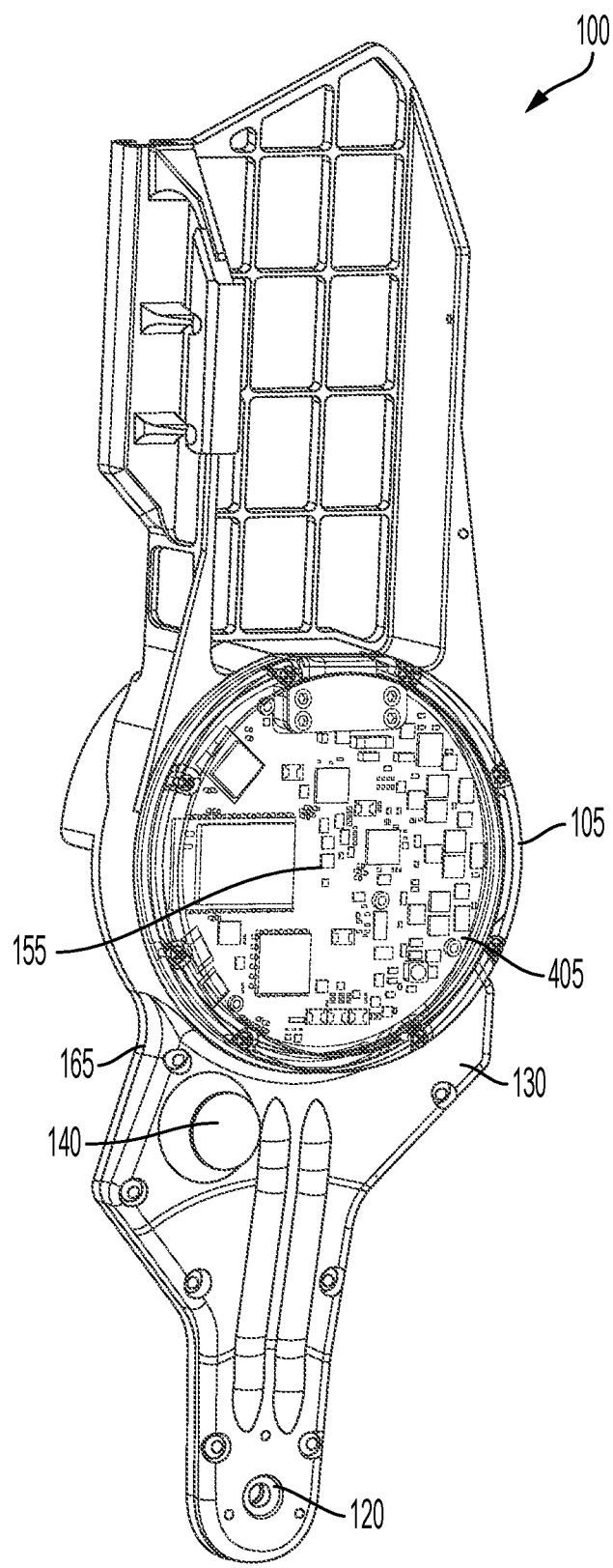
FIG. 4 illustrates a schematic diagram of an exoskeleton and internal parts, according to an embodiment.
Figure 5:
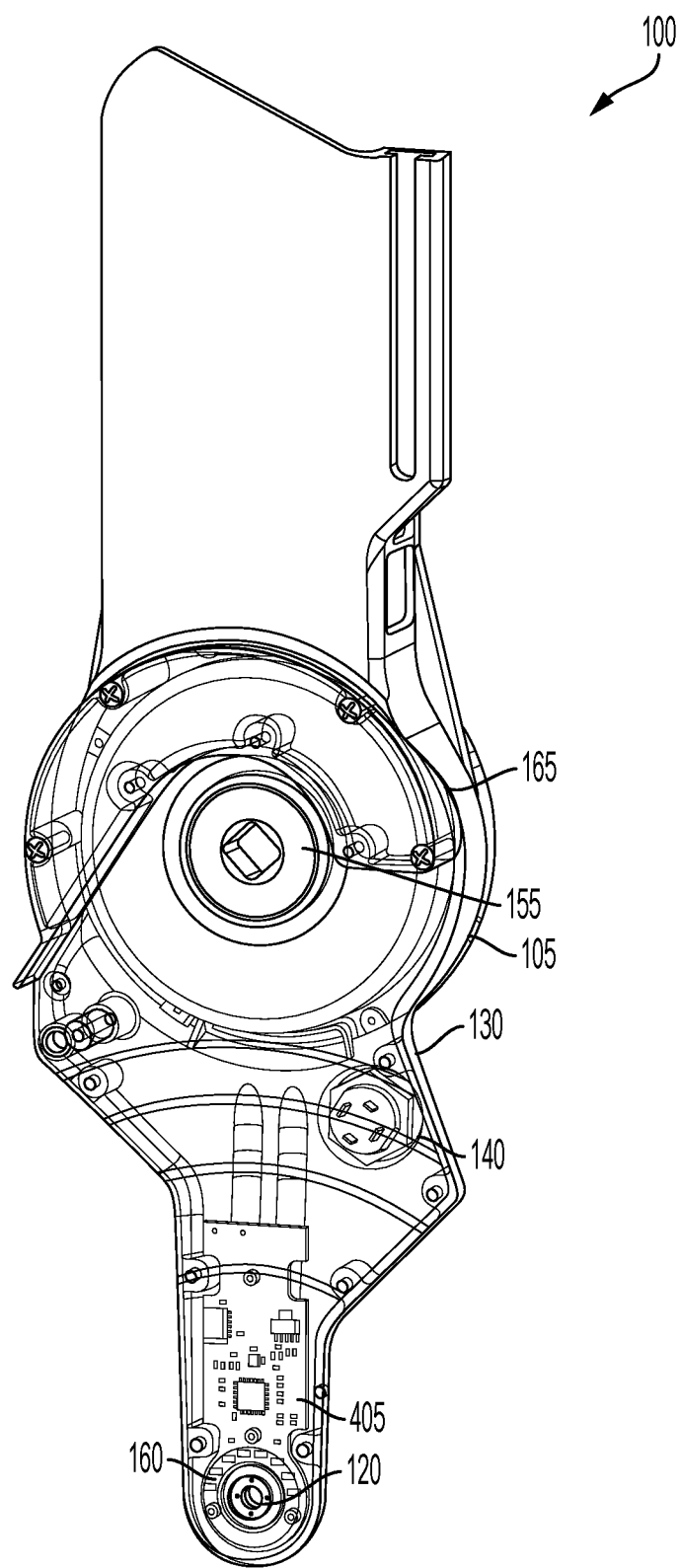
FIG. 5 illustrates a schematic diagram of an exoskeleton and internal parts, according to an embodiment.

FIG. 4 and FIG. 5 illustrate schematic diagrams of the exoskeleton 100 and internal parts. The exoskeleton 100 can include the one or more housings 105, the ankle joint component 120, the actuator 130, the power button 140, the rotary encoder 155, the second rotary encoder 160, and the sealant 165 as described above. The internal parts can include an electronic circuit (e.g., circuitry, electronics 405). The electronic circuit can include individual electronic components (e.g., resistors, transistors, capacitors, inductors, diodes, processors, or controllers). The power button 140 can be electrically connected to the electronic circuit. The electronics 405 can be located behind the electric motor. The electronics 405 can include the main electronics board. The rotary encoder 155 can be located between the motor and electronics 405.

Figure 6:
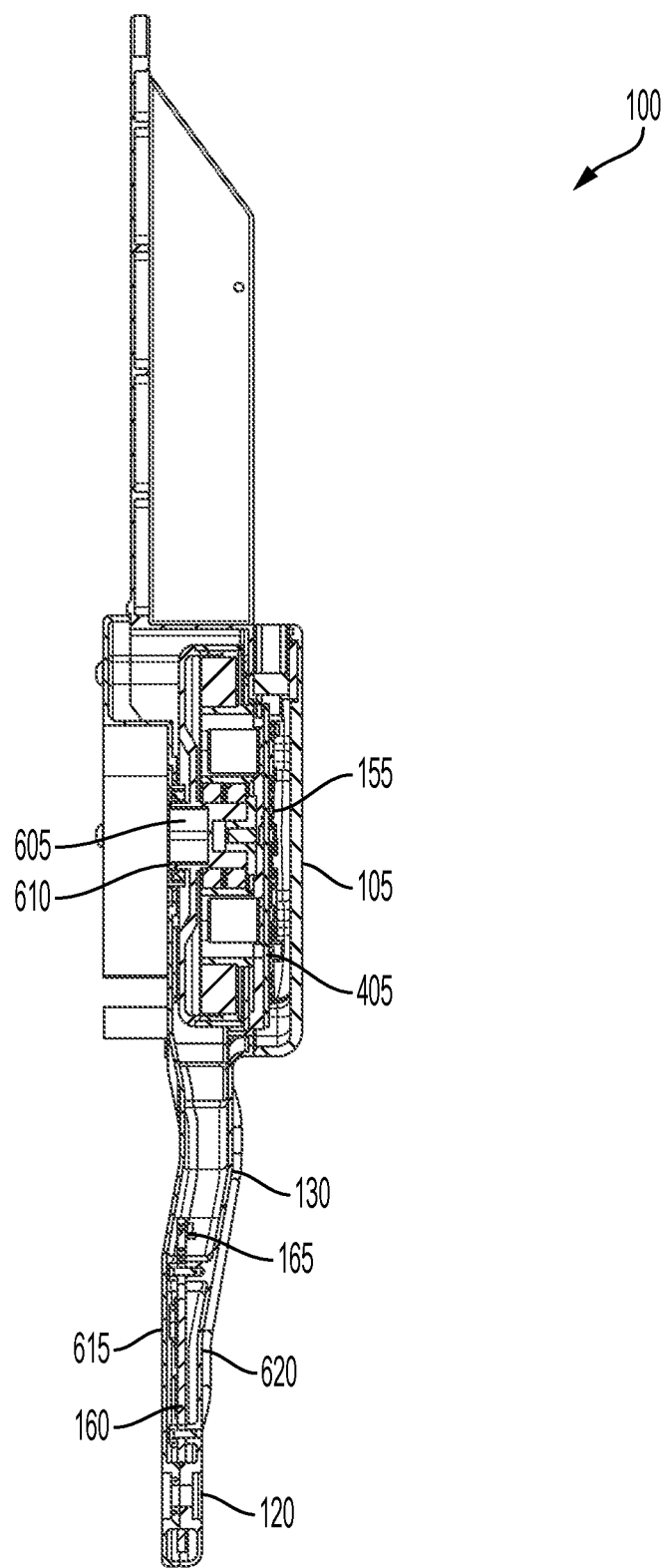
FIG. 6 illustrates a side view of an exoskeleton, according to an embodiment.

FIG. 6 illustrates a side view of the exoskeleton 100. The exoskeleton 100 can include the one or more housings 105, ankle joint component 120, the actuator 130, the rotary encoder 155, the second rotary encoder 160, the sealant 165, and electronics 405 as described above. The exoskeleton 100 can include an output shaft 605 (e.g., motor rotor, spool shaft, pinion gear, spur gear, or toothed pulley). The output shaft 605 can be coupled to the electric motor. The output shaft 605 can extend through a bore 610 in a housing of the one or more housings 105 enclosing the electric motor. The bore 610 can receive the output shaft 605. An encoder chip can be located on the electronics board on a first side of the electric motor. The encoder chip can measure the angular position of the rotary encoder 155. The exoskeleton 100 can include a transmission (e.g., gearbox) configured to couple the output shaft 605 to the electric motor. The transmission can include a machine in a power transmission system. The transmission can provide controlled application of power. The output shaft 605 can be integrated into the motor rotor. The output shaft 605 can be part of a mechanism (e.g., gears, belts, linkage, or change). An ankle shaft can extend through the second rotary encoder 160 which can increase the structural integrity of the exoskeleton 100.

The exoskeleton 100 can include a first component of the fitted structure 615 (e.g., first clamshell structure). The exoskeleton 100 can include a second component of the fitted structure 620 (e.g., second clamshell structure). The first component of the fitted structure 615 can be coupled with the second component of the fitted structure 620. The first component of the fitted structure 615 can be attached to the second component of the fitted structure 620 via the sealant 165 (e.g., adhesive sealant). The first component of the fitted structure 615 can be coupled to the second component of the fitted structure 620 such that the fitting prevents or decreases a rate of water flow into the interior of the exoskeleton 100. The fitted structure can include two or more components such that the assembly components prevents or decreases a rate of water flow into the interior of the exoskeleton 100. The first component of the fitted structure 615 and the second component of the fitted structure 620 can be stationary components. The number of individual components of the fitted structure can be minimized to decrease the number of possible entry points for water to enter the exoskeleton 100. The possible entry points can include seams and/or moving parts of the exoskeleton 100. The seams can be permanently sealed via the sealant 165. The moving parts can be sealed via the one or more of the seals 700 described herein.

An adhesive sealant (e.g., super glue, epoxy resin, or polyvinyl acetate) can be placed between the first component of the fitted structure 615 and the second component of the fitted structure 620. The adhesive sealant can prevent or decrease the rate of water flow through the seam between the first component of the fitted structure 615 and the second component of the fitted structure 620 into the interior of the exoskeleton 100. The adhesive sealant can be placed under the electronics cover. The adhesive sealant can prevent or decrease the rate of water flow through the seam between the electronics cover and the exoskeleton one or more housings 105 into the interior of the exoskeleton 100.

A gasket can be placed between the first component of the fitted structure 615 and the second component of the fitted structure 620. The gasket can be placed in the seam between the first component of the fitted structure 615 and the second component of the fitted structure 620. The gasket can prevent or decrease the rate of water flow through the seam between the first component of the fitted structure 615 and the second component of the fitted structure 620.

Figure 7:
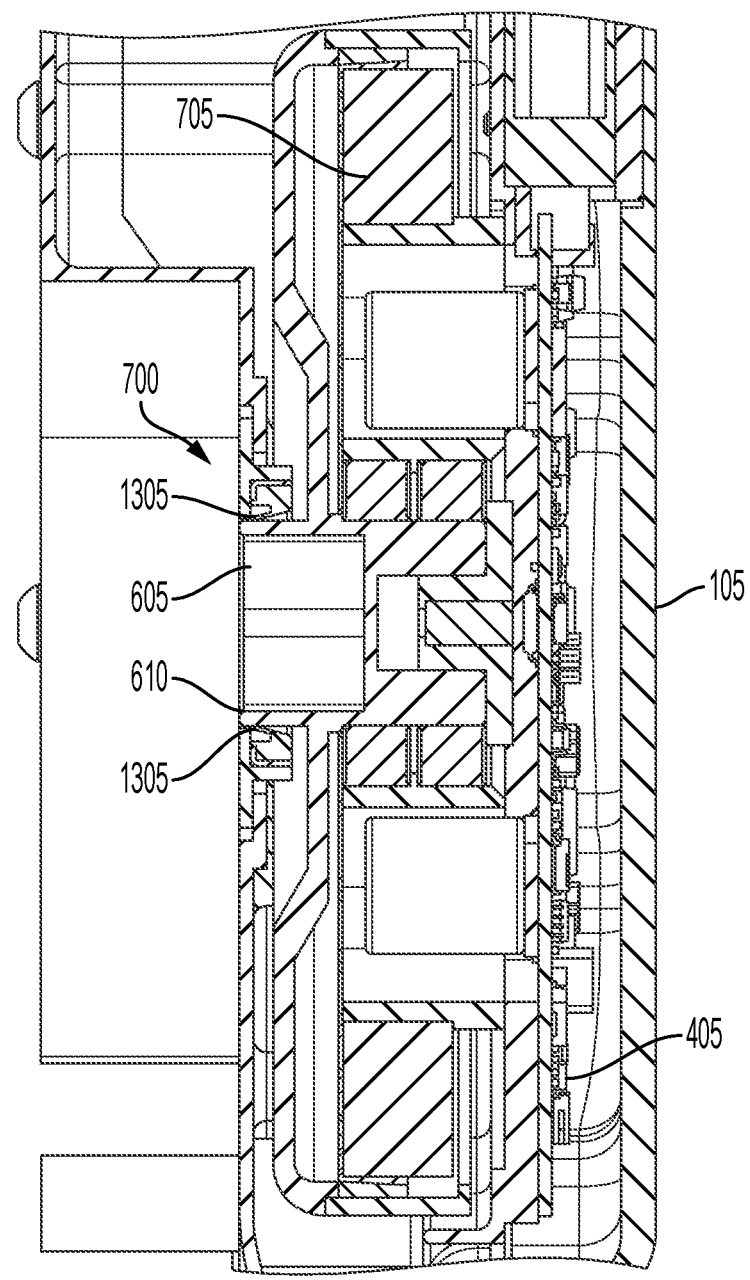
FIG. 7 illustrates a schematic diagram of a seal, according to an embodiment.

FIG. 7 illustrates a schematic diagram of a seal 700 (e.g., shaft seal 1305). The seal 700 can be part of the exoskeleton 100. The seal 700 can include the output shaft 605. The output shaft 605 can be coupled to the electric motor. The seal 700 can include the bore 610. The exoskeleton 100 can include the seal 700 in contact with the output shaft 605 and a portion of the housing including the bore 610. The output shaft 605 can extend through the bore 610 in a housing of the one or more housings 105 enclosing the electric motor. The bore 610 can receive the output shaft 605. A magnet can be located on a first side of the electric motor. An encoder chip can be located on the electronics board on the first side of the electric motor. The encoder chip can measure the angular position of the rotary encoder 155. An ankle shaft can extend through the second rotary encoder 160 which can increase the structural integrity of the exoskeleton 100.

The exoskeleton 100 can include a transmission (e.g., gearbox) configured to couple the output shaft 605 to the electric motor. The seal 700 can prevent an ingress of water into the one or more housings 105. The seal 700 can be installed and aligned to the output shaft 605. The exoskeleton 100 can include a motor stator 705. The motor stator 705 can include a stationary element. The motor stator 705 can provide a rotating magnetic field that drives a rotating armature. The motor stator 705 can convert a rotating magnetic field to electric current. The output shaft 605 can be sealed with an elastomeric lip that applies pressure radially to the seal 700. The output shaft 605 can be a moving part within the exoskeleton 100. Grease can be located between the seal 700 and the output shaft 605.

Figure 8:
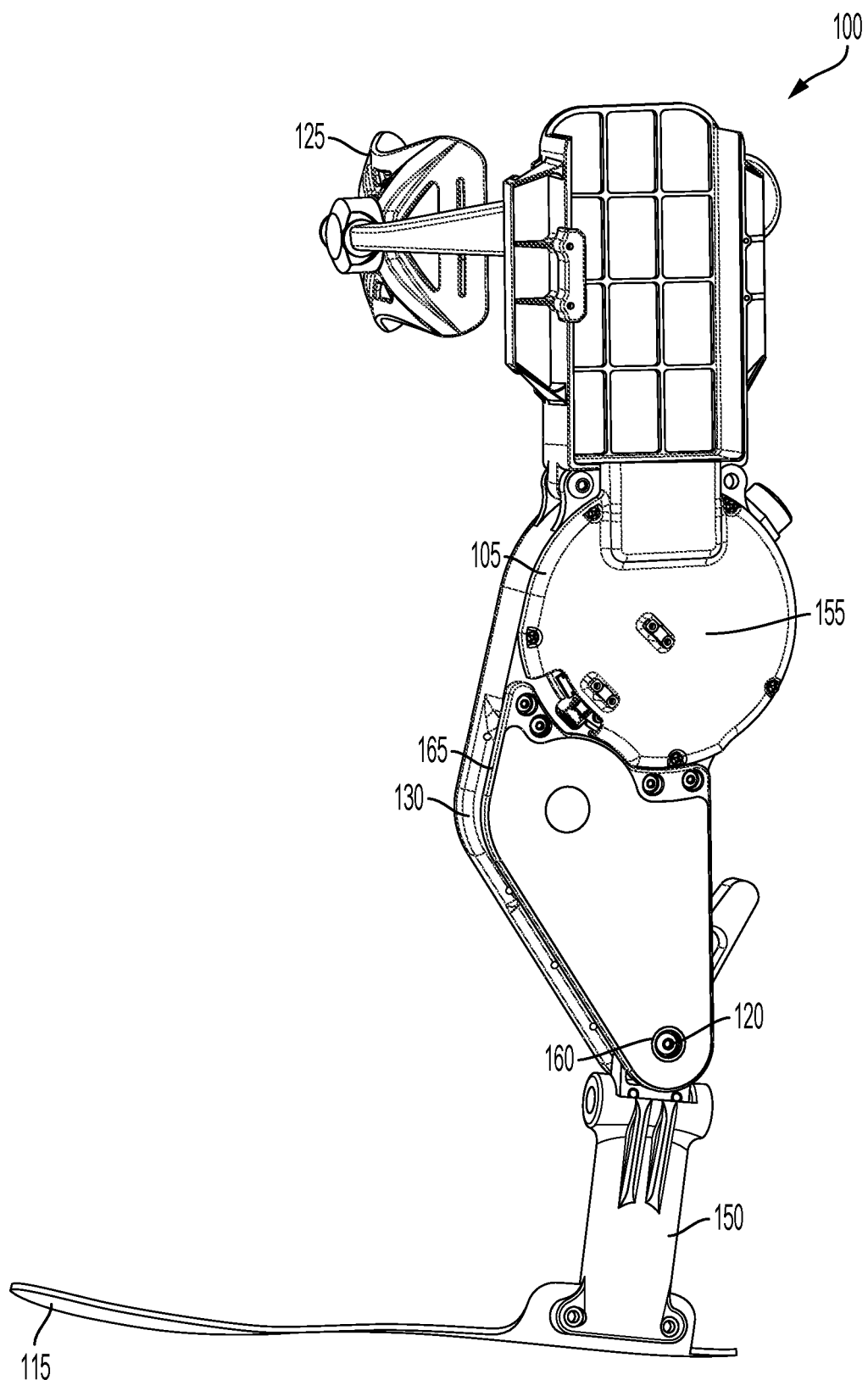
FIG. 8 illustrates a schematic diagram of an exoskeleton, according to an embodiment.

FIG. 8 illustrates a schematic diagram of the exoskeleton 100. The exoskeleton 100 can include the one or more housings 105, the footplate 115, the ankle joint component 120, the shin pad 125, the actuator 130, the post 150, the rotary encoder 155, the second rotary encoder 160, and the sealant 165 as described above. The one or more housings 105 can be coupled to the shin pad 125. The post 150 can couple the ankle joint component 120 with the footplate 115. The actuator 130 can include the one or more housings 105, the footplate 115, the ankle joint component 120, and the post 150. The rotary encoder 155 can measure an angle of the electric motor. The second rotary encoder 160 can measure an angle of the ankle joint.

Figure 9:
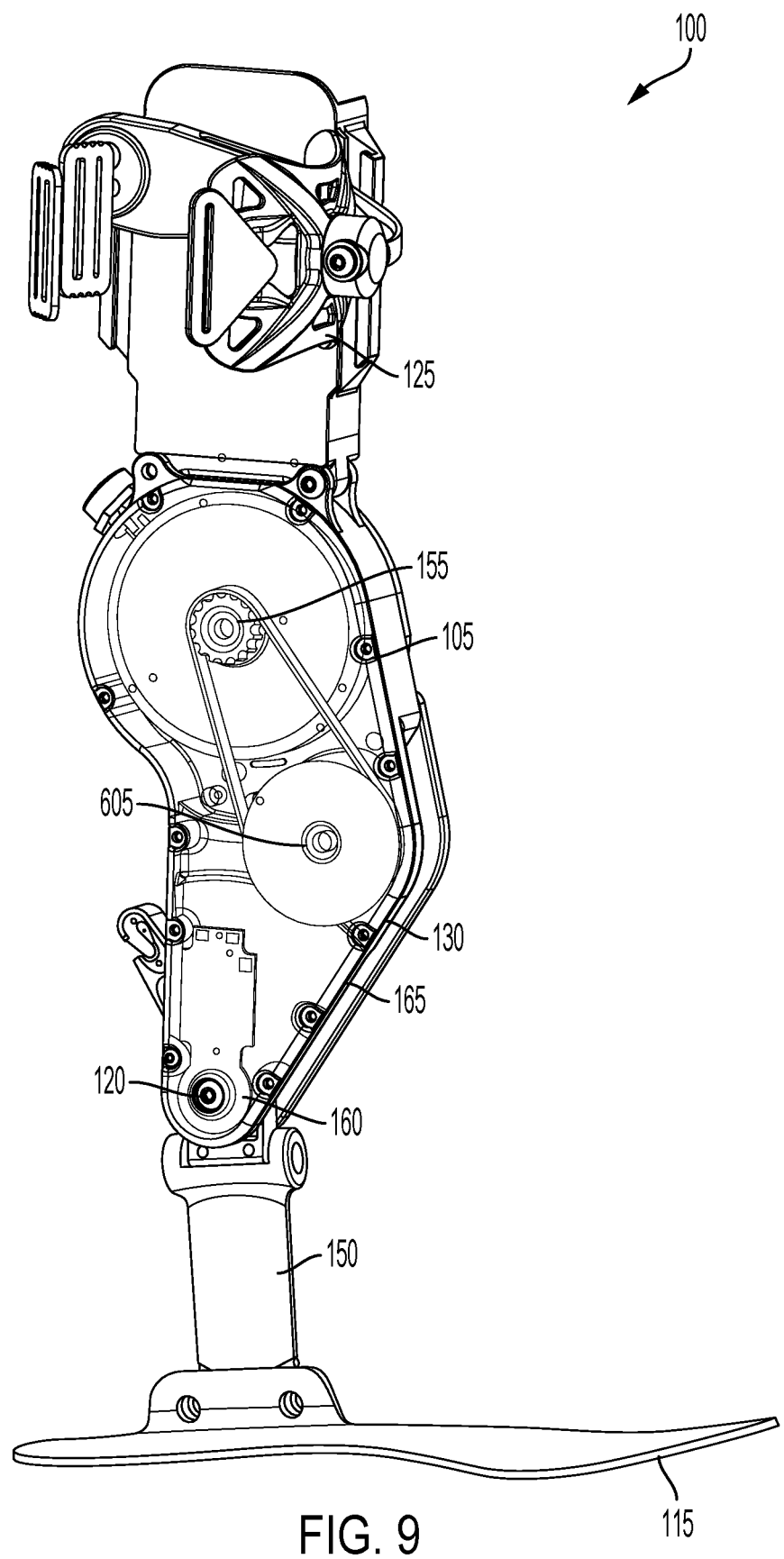
FIG. 9 illustrates a schematic diagram of an exoskeleton and internal parts, according to an embodiment.
Figure 10:
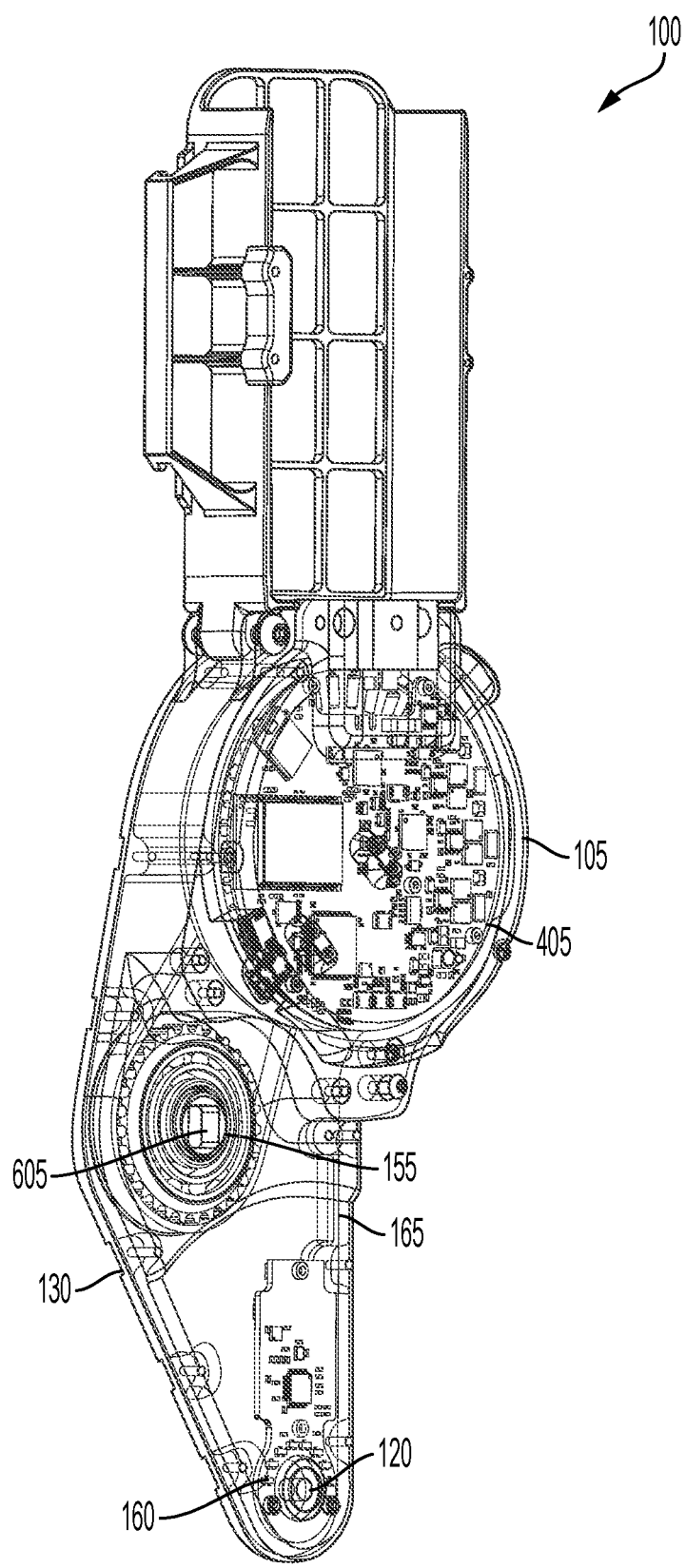
FIG. 10 illustrates a schematic diagram of an exoskeleton and internal parts, according to an embodiment.

FIG. 9 and FIG. 10 illustrate schematic diagrams of the exoskeleton 100 and internal parts. The exoskeleton 100 can include the one or more housings 105, the footplate 115, the ankle joint component 120, shin pad 125, the actuator 130, the post 150, the rotary encoder 155, the second rotary encoder 160, the sealant 165, and electronics 405 as described above. The internal parts can include an electronic circuit (e.g., circuitry). The electronic circuit can include individual electronic components (e.g., resistors, transistors, capacitors, inductors, diodes, processors, or controllers). The motor rotor can be connected to the output shaft 605.

Figure 11:
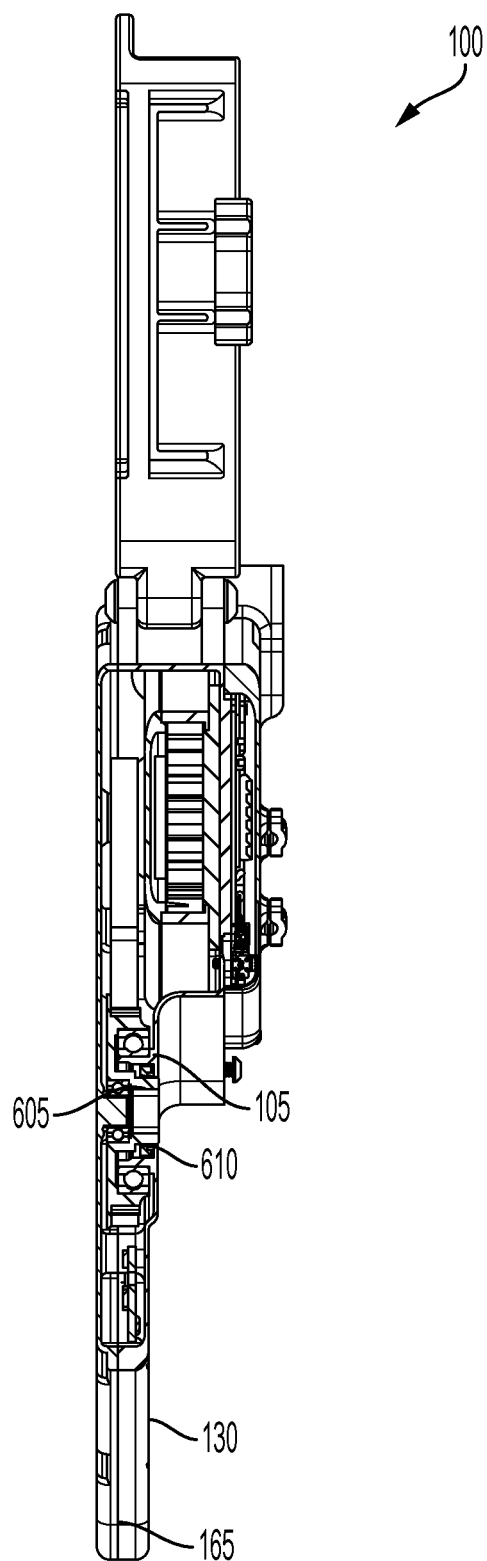
FIG. 11 illustrates a side view of an exoskeleton, according to an embodiment.

FIG. 11 illustrates a side view of the exoskeleton 100. The exoskeleton 100 can include the one or more housings 105, the actuator 130, the rotary encoder 155, the second rotary encoder 160, and the sealant 165, the output shaft 605, and the bore 610 as described above. The exoskeleton 100 can include an output shaft 605 (e.g., motor rotor). The output shaft 605 can be coupled to the electric motor. The output shaft 605 can extend through a bore 610 in a housing of the one or more housings 105 enclosing the electric motor. The bore 610 can receive the output shaft 605. A magnet can be located on a first side of the electric motor. An encoder chip can be located on the electronics board on the first side of the electric motor. The encoder chip can measure the angular position of the rotary encoder 155. An ankle shaft can extend through the second rotary encoder 160 which can increase the structural integrity of the exoskeleton 100. The exoskeleton 100 can include a transmission (e.g., gearbox) configured to couple the output shaft 605 to the electric motor. The transmission can include a machine in a power transmission system. The transmission can provide controlled application of power.

Figure 12:
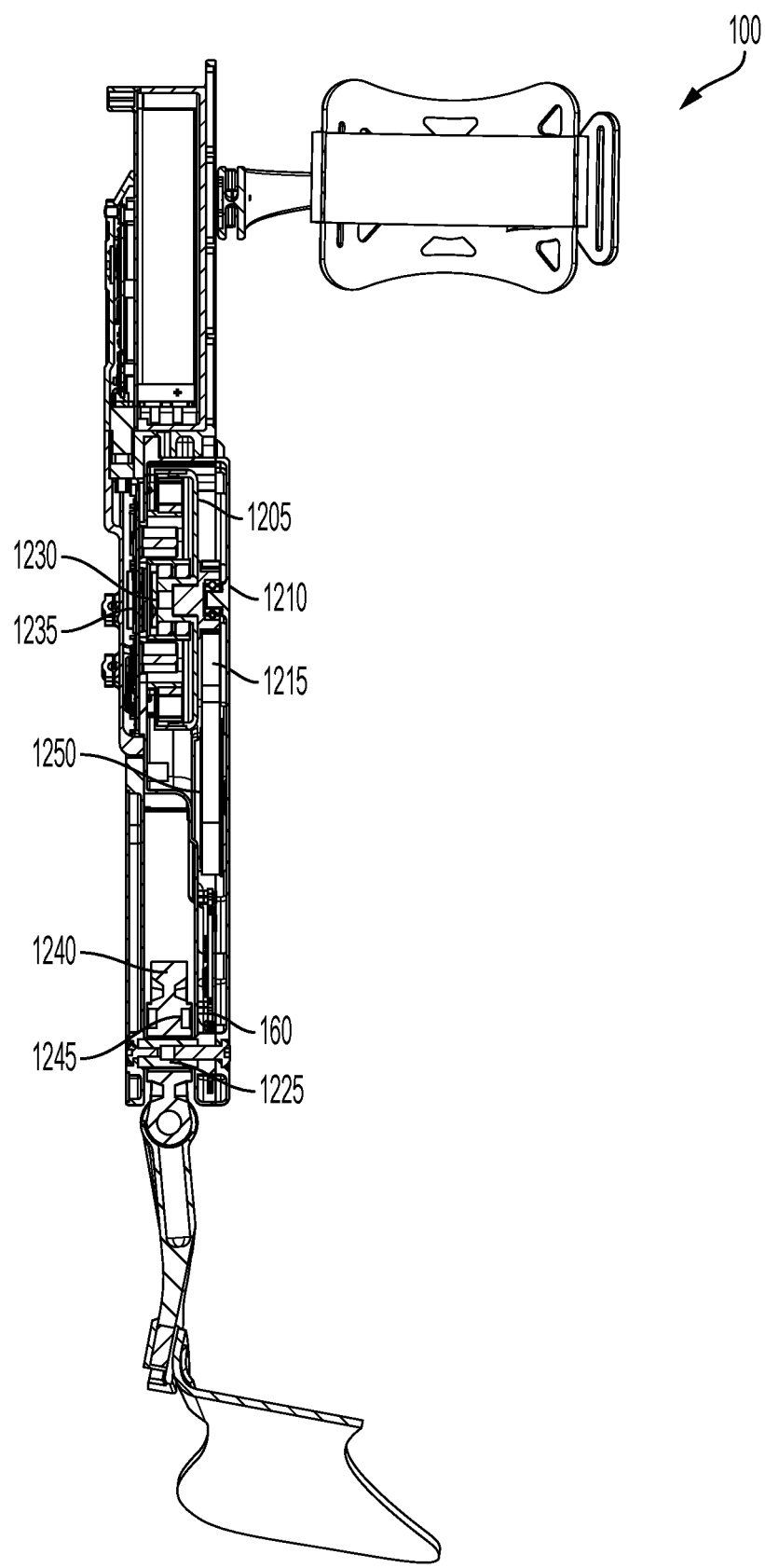
FIG. 12 illustrates a side view of an exoskeleton, according to an embodiment.

FIG. 12 illustrates a side view of an exoskeleton 100. The exoskeleton 100 can include a motor 1205 (e.g., electric motor), a motor timing pulley 1210 (e.g., timing pulley), a motor timing belt 1215 (e.g., timing belt), the second rotary encoder 160 (e.g., an ankle encoder PCB, ankle encoder printed circuit board, second rotary encoder PCB, or ankle encoder), an ankle shaft 1225, a motor encoder magnet 1230, a motor encoder 1235, a lever arm 1240 (e.g., ankle lever), and an ankle encoder magnet 1245. The ankle shaft 1225 can extend through the second rotary encoder 160 to increase the structural integrity of the exoskeleton 100. The motor timing belt 1215 can be coupled to a sprocket 1250. The sprocket 1250 can be coupled with a spool (e.g., spool 1315). The motor encoder magnet 1230 can be located on the first side of the electric motor.

Figure 13:
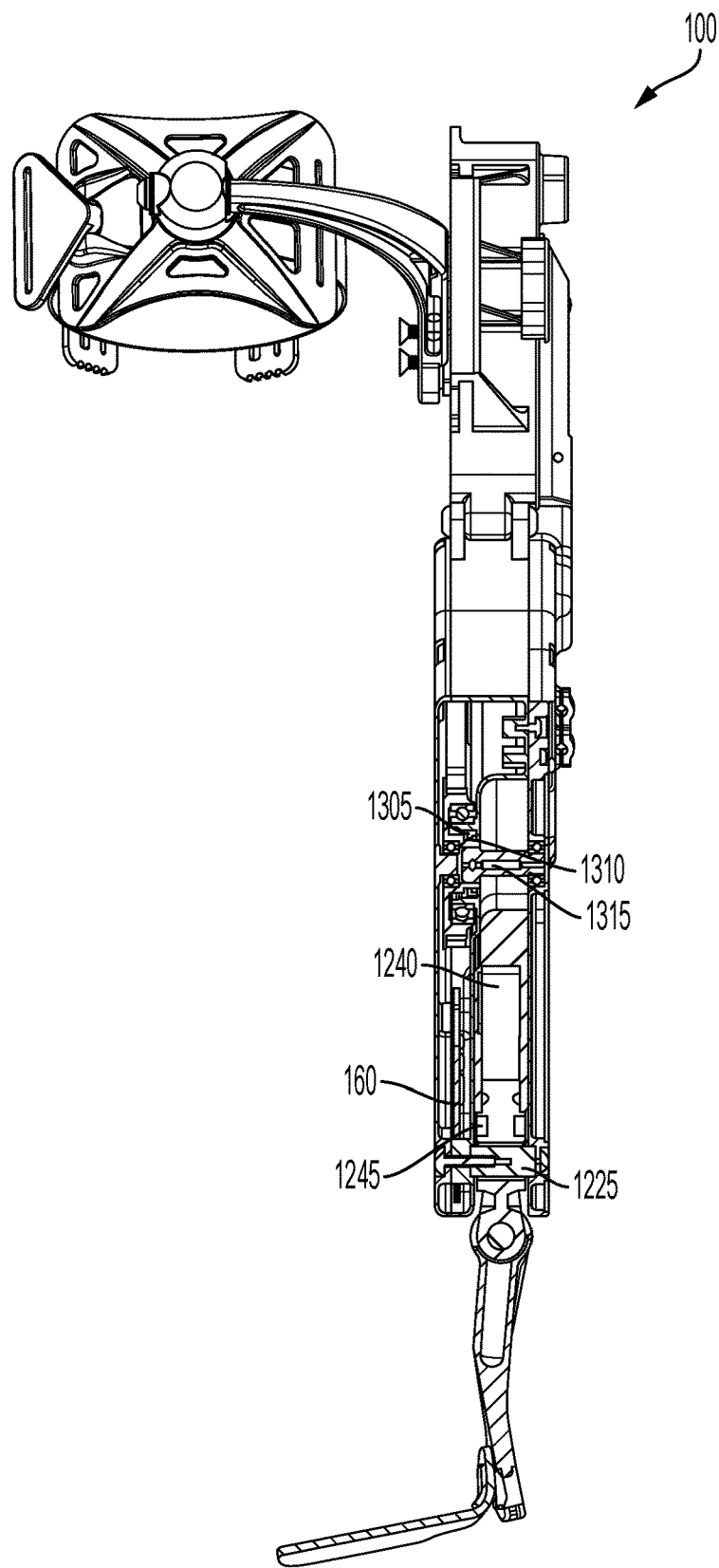
FIG. 13 illustrates a side view of an exoskeleton, according to an embodiment.

FIG. 13 illustrates a side view of an exoskeleton 100. The exoskeleton 100 can include the second rotary encoder 160, the ankle shaft 1225, the lever arm 1240, and the ankle encoder magnet 1245. The exoskeleton 100 can include the elastomeric shaft seal 1305. Grease can be applied to the elastomeric shaft seal 1305. The exoskeleton 100 can include the sealing surface 1310 on the output shaft 605. Grease can be applied at the sealing surface 1310. The grease can prevent an ingress of water into the exoskeleton 100. The exoskeleton 100 can include a spool 1315 (e.g., spool shaft). The spool 1315 can be coupled with the actuator belt 135.

Figure 14:
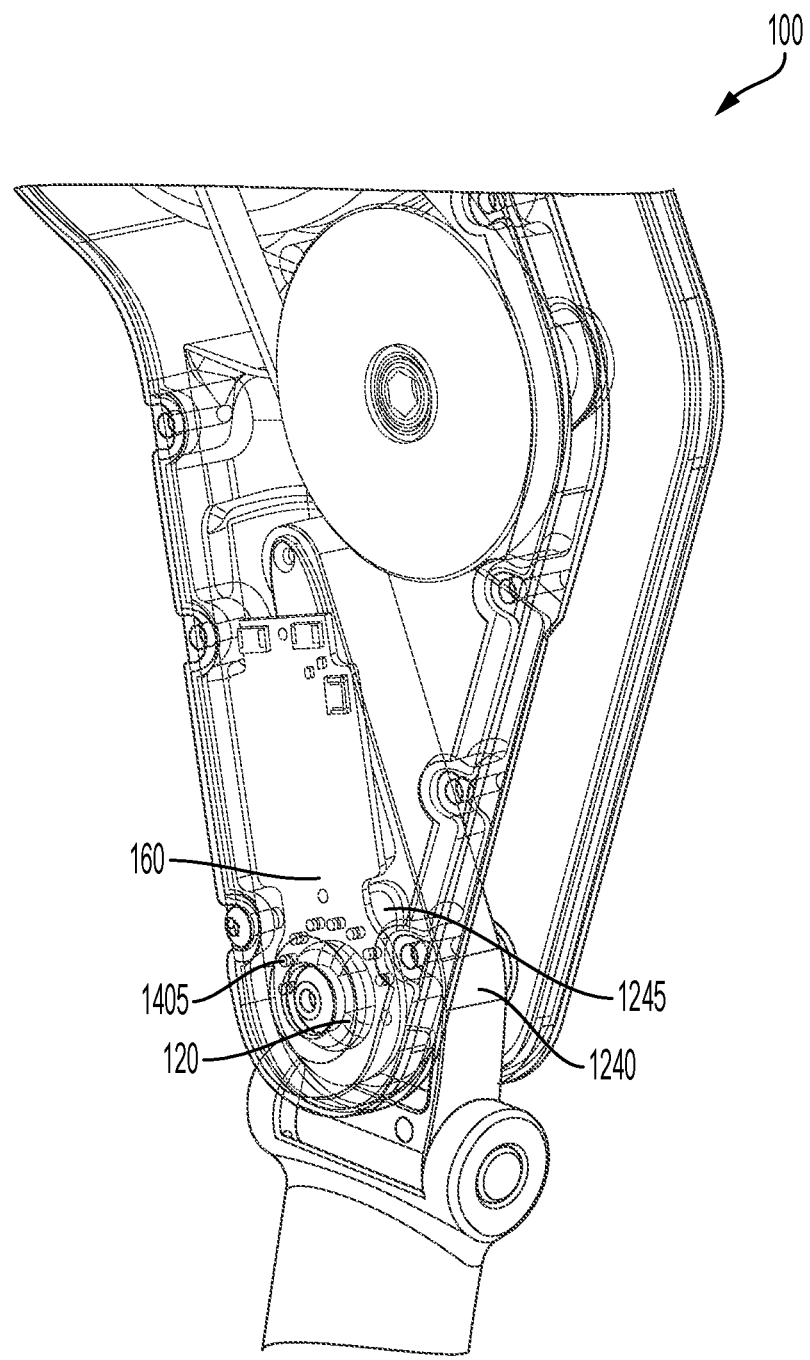
FIG. 14 illustrates a schematic diagram of an exoskeleton, according to an embodiment.

FIG. 14 illustrates a schematic diagram of an exoskeleton 100. The exoskeleton 100 can include the ankle joint component 120, the second rotary encoder 160, the lever arm 1240, and the ankle encoder magnet 1245. The position of the ankle encoder magnet 1245 relative to the second rotary encoder 160 can indicate an angle of the ankle joint. The second rotary encoder 160 can measure an angle of the ankle joint. The second rotary encoder 160 can include a first component (e.g., sensor 1405) enclosed in the one or more housings 105 and in communication with the electronic circuitry. The second rotary encoder 160 can include a second component (e.g., ankle encoder magnet 1245) located outside the one or more housings 105 and configured to interact with the first component. The first component of the second rotary encoder 160 can include a sensor (e.g., Hall-effect sensor). The second rotary encoder 160 can include one or more sensors. The one or more sensors can be arranged on a line (e.g., straight line, or curved line). The second rotary encoder 160 can be configured to determine the angle of the ankle joint using the one or more sensors. The second rotary encoder 160 can determine the angle of the ankle joint based on an interaction between the sensor 1405 and the ankle encoder magnet 1245. The exoskeleton 100 can include a housing (e.g., aluminum housing) separating the sensor 1405 from the ankle encoder magnet 1245. The one or more housings 105 can include an aluminum housing. The aluminum housing can separate the first component from the second component. The aluminum housing can separate the sensor 1405 from the ankle encoder magnet 1245. The ankle encoder magnet 1245 can include a permanent magnet.

Figure 15:
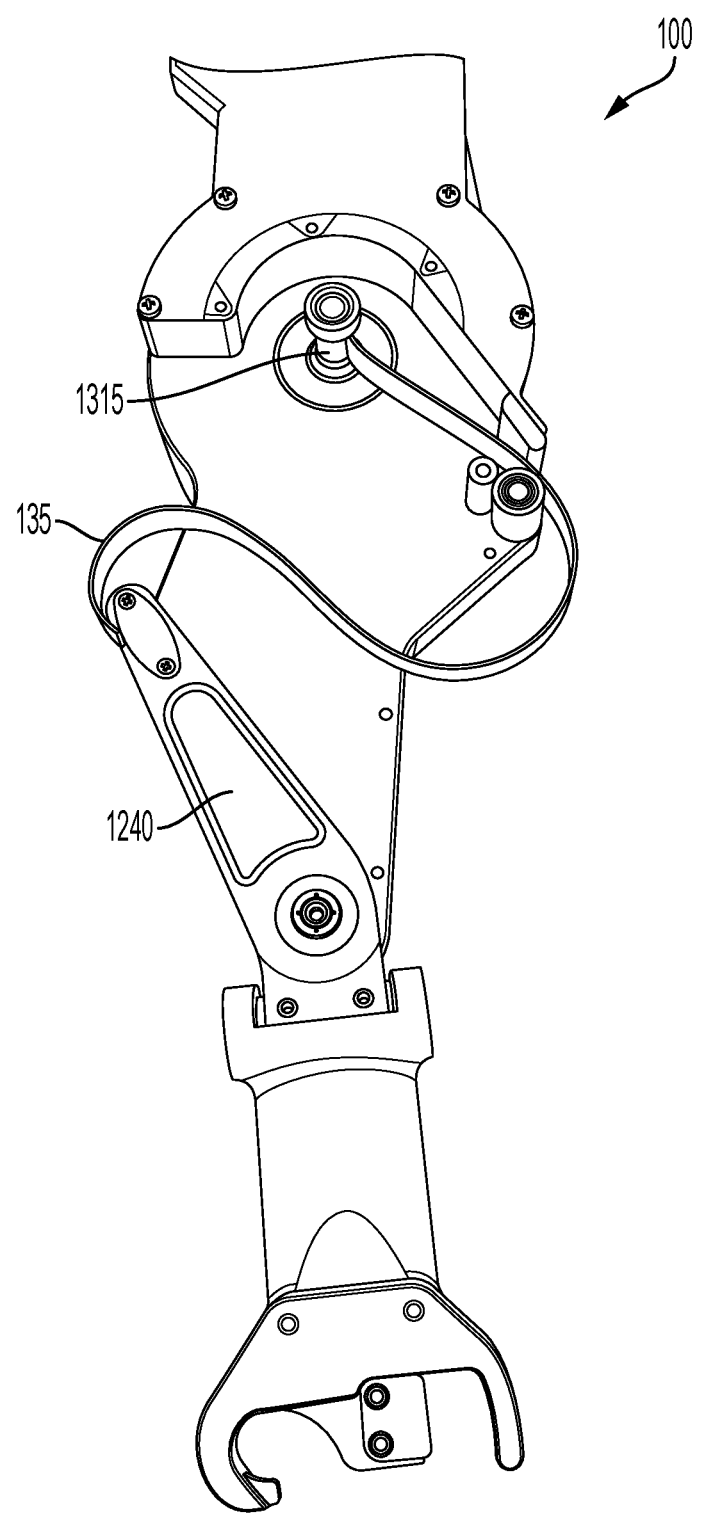
FIG. 15 illustrates a schematic diagram of an exoskeleton, according to an embodiment.

FIG. 15 illustrates a schematic diagram of an exoskeleton 100. The exoskeleton 100 can include the lever arm 1240, the actuator belt 135, and the spool 1315. The actuator belt 135 can be coupled with the spool 1315. For example, the actuator belt 135 can be removably attached to the spool 1315. The spool 1315 can wind the actuator belt 135 to apply a force to the lever arm 1240. The rotation of the spool 1315 can translate to rotation (e.g., movement) of the lever arm 1240 about the ankle joint component 120. The rotation of the spool 1315 can be coupled to rotation of the lever arm 1240 via the actuator belt 135. The actuator belt 135 can be coupled with the lever arm 1240. For example, the actuator belt 135 can be removably attached to the lever arm 1240. The actuator belt 135 can extend from one end of the lever arm 1240 to the spool 1315.

Figure 16:
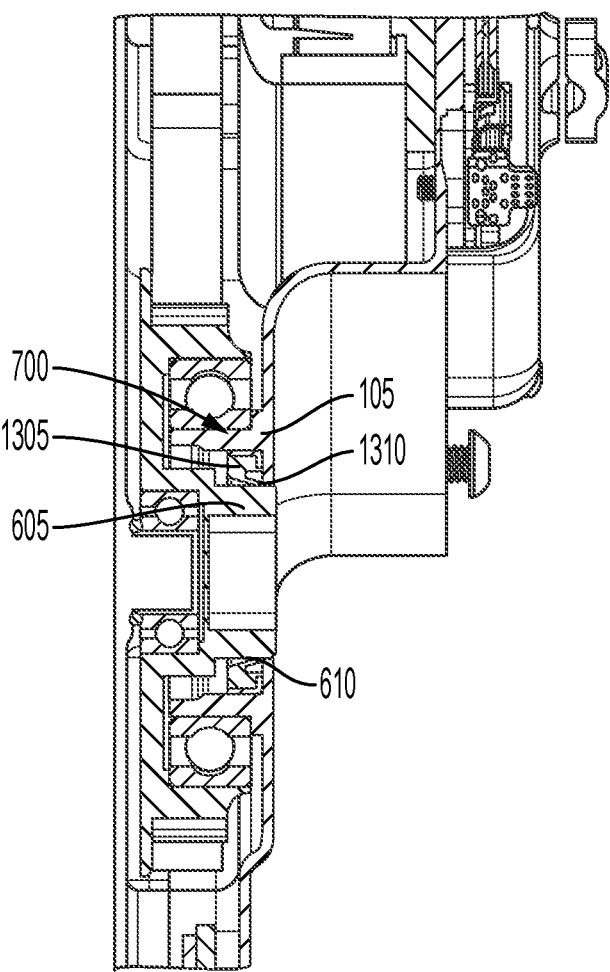
FIG. 16 illustrates a schematic diagram of a seal, according to an embodiment.

FIG. 16 illustrates a schematic diagram of the seal 700. The seal 700 can be part of the exoskeleton 100. The seal 700 can include the output shaft 605. The output shaft 605 can be coupled to the electric motor. The seal 700 can include the bore 610. The exoskeleton 100 can include the seal 700 in contact with the output shaft 605 and a portion of the housing including the bore 610. The output shaft 605 can extend through the bore 610 in a housing of the one or more housings 105 enclosing the electric motor. The bore 610 can receive the output shaft 605. A magnet can be located on a first side of the electric motor. An encoder chip can be located on the electronics board on the first side of the electric motor. The encoder chip can measure the angular position of the rotary encoder 155. An ankle shaft can extend through the second rotary encoder 160 which can increase the structural integrity of the exoskeleton 100. The exoskeleton 100 can include a transmission (e.g., gearbox) configured to couple the output shaft 605 to the electric motor. The seal 700 can prevent an ingress of water into the one or more housings 105. The seal 700 can include waterproofing between the motor and a last stage of transmission. The output shaft 605 can connect the motor to the last stage of transmission. The seal 700 can include the elastomeric shaft seal 1305. Grease can be applied to the elastomeric shaft seal 1305. The seal 700 can include the sealing surface 1310 on the output shaft 605. Grease can be applied at the sealing surface 1310.

Figure 17:
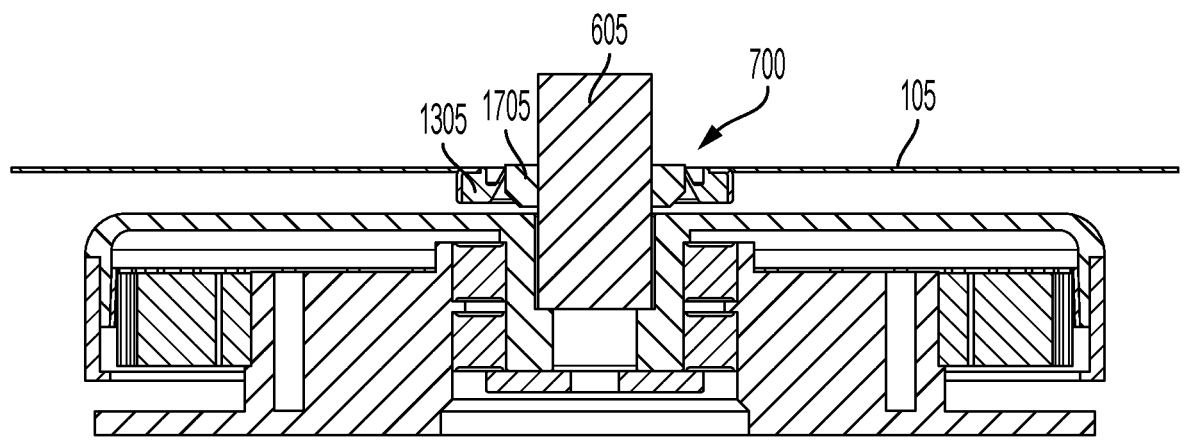
FIG. 17 illustrates a schematic diagram of a seal, according to an embodiment.

FIG. 17 illustrates a schematic diagram of the seal 700. The seal 700 can be in contact with the output shaft 605. The seal 700 can include a mechanical seal. The seal 700 can contact a rotating surface. The rotating surface can include the output shaft 605. The seal 700 can seal the internal components in the interior of the exoskeleton 100. The seal 700 can prevent an ingress of water into the internal components. The output shaft 605 can be statically coupled with a collar 1705. The collar 1705 can contact the elastomeric shaft seal 1305. Grease can be applied to the elastomeric shaft seal 1305. The seal 700 can be precision manufactured. The seal 700 can be a dynamic seal.

Figure 18:
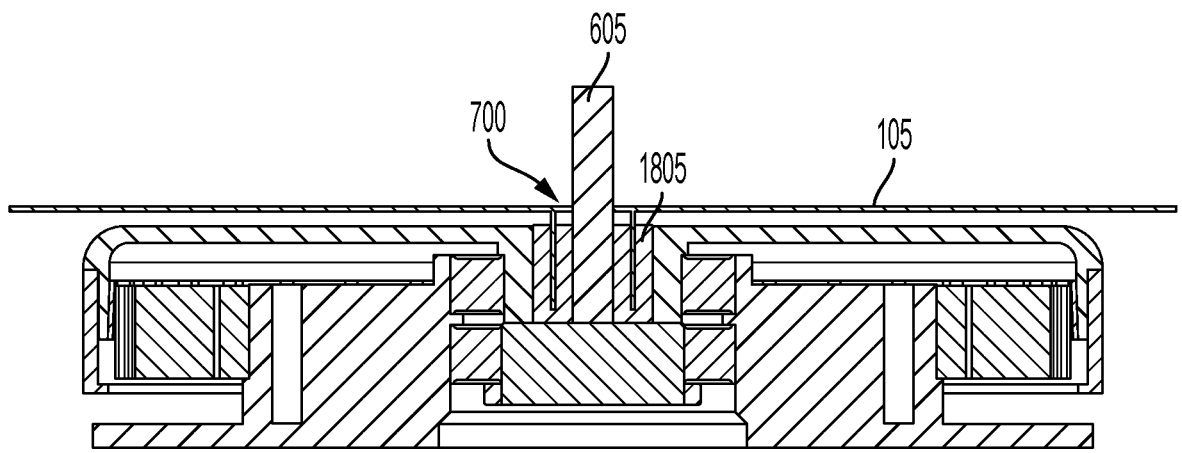
FIG. 18 illustrates a schematic diagram of a seal, according to an embodiment.

FIG. 18 illustrates a schematic diagram of the seal 700. The seal 700 can include grease 1805 (e.g., sealing grease, oil seal, or grease seal). The grease 1805 can provide an airtight fit around sealing surfaces (e.g., the one or more housings 105 and the output shaft 605). The grease 1805 can close spaces between stationary components (e.g., one or more housings 105) and moving components (e.g., output shaft 605). The grease 1805 can prevent an ingress of water into the exoskeleton 100 while reducing friction between stationary component and moving components. The seal 700 can include a gasket. The seal 700 can include a packing material (e.g., grease impregnated wool, or rubber). The seal 700 can seal the internal components in the interior of the exoskeleton 100. The seal 700 can prevent an ingress of water into the internal components.

Figure 19:
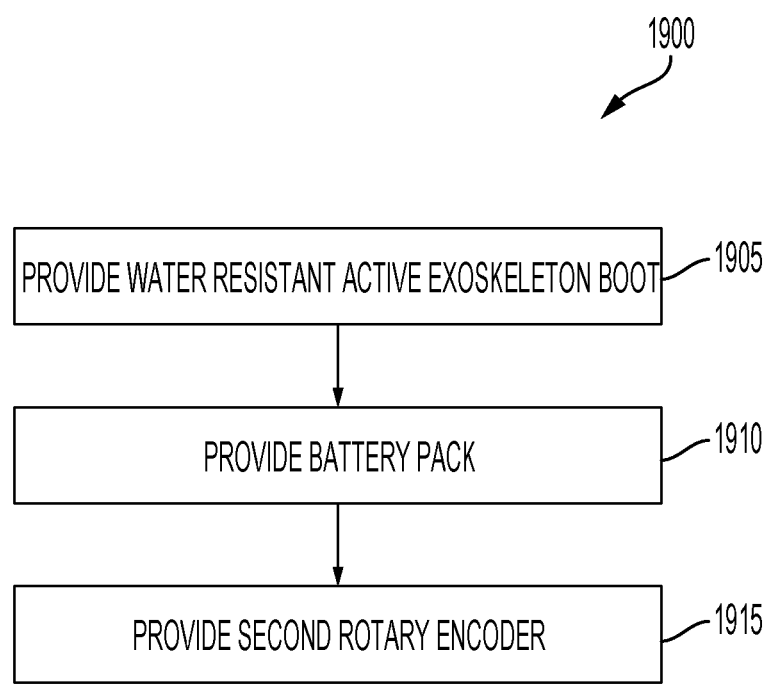
FIG. 19 illustrates a method of augmenting user motion, according to an embodiment.

FIG. 19 illustrates a method 1900 of augmenting user motion. The method 1900 can include providing, to a user, a water resistant active exoskeleton boot (BLOCK 1905). The water resistant active exoskeleton boot can include a shin pad to be coupled to a shin of a user and at least one housing of one or more housings. The one or more housings can enclose electronic circuitry and an electric motor that can generate torque about an axis of rotation of an ankle joint of the user. A sealant can be placed in contact with the one or more housings to close the one or more housings and prevent an ingress of water into the one or more housings. The water resistant active exoskeleton boot can include an output shaft coupled to the electric motor and extending through a bore in a housing of the one or more housings enclosing the electric motor. The water resistant active exoskeleton boot can include a seal in contact with the output shaft and a portion of the housing including the bore. The seal can prevent an ingress of the water into the one or more housings. The water resistant active exoskeleton boot can include a rotary encoder enclosed within the one or more housings to measure an angle of the electric motor. The electronic circuitry can receive, from the rotary encoder, an indication of the angle of the electric motor and can control, based on the indication of the angle of the electric motor, operation of the electric motor to generate torque about the axis of rotation of the ankle joint of the user.

In some embodiments, the seal in contact with the output shaft includes grease. The sealant used to close the one or more housings can include an adhesive sealant. The sealant used to close the one or more housings can include epoxy and can permanently close the one or more housings.

The method 1900 can include providing a battery pack coupled to the one or more housings below a knee of the user (BLOCK 1910). The method 1900 can include providing a second rotary encoder 160 to measure an angle of the ankle joint (BLOCK 1915). The second rotary encoder 160 can include a first component enclosed in the one or more housings and can be in communication with the electronic circuitry. The second rotary encoder 160 can include a second component located outside the one or more housings and configured to interact with the first component.

Figure 20:
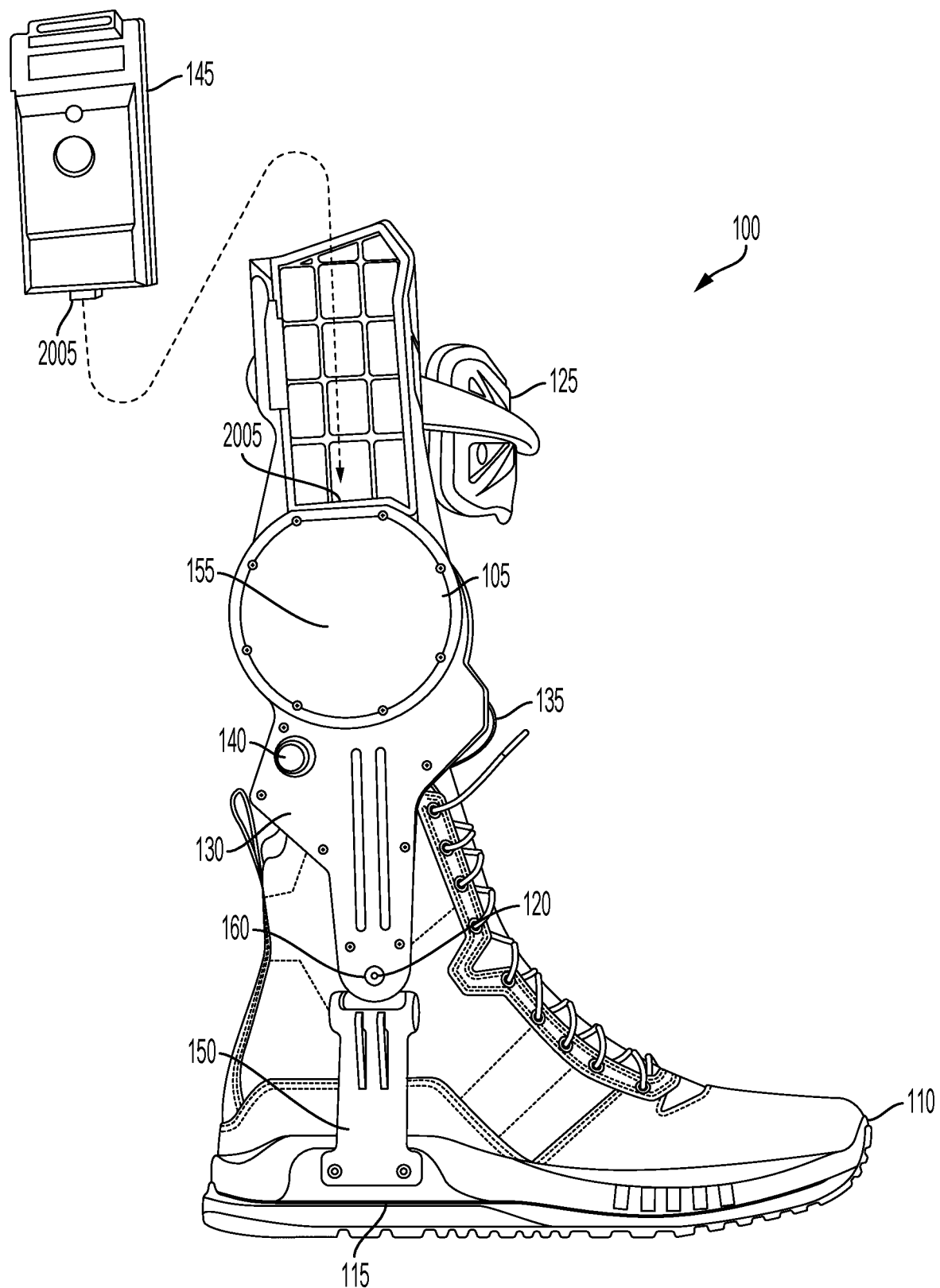
FIG. 20 illustrates a schematic diagram of an exoskeleton, according to an embodiment.

FIG. 20 illustrates a schematic diagram of the exoskeleton 100. The exoskeleton 100 includes the one or more housings 105, the boot 110 the footplate 115, the ankle joint component 120, shin pad 125, the actuator 130, the actuator belt 135, the power button 140, the battery 145, the post 150, the rotary encoder 155, and the second rotary encoder 160. The battery 145 can include a power connector 2005. The power connector 2005 can couple (e.g., connect) the battery 145 with the electronics 405. The power connector 2005 can couple the battery 145 with the one or more housings 105. The battery 145 can be inserted into the exoskeleton 100. The battery 145 can include a sealed battery. The battery 145 can coupled with the exoskeleton 100 via a waterproof or water resistant connection. The battery 145 can connect locally (e.g., proximate) to the exoskeleton 100 such that a wire is not needed to run from the battery 145 to the electronics 405.

Embodiments of the subject matter and the operations described in this specification can be implemented in digital electronic circuitry, or in computer software, firmware, or hardware, including the structures disclosed in this specification and their structural equivalents, or in combinations of one or more of them. The subject matter described in this specification can be implemented as one or more computer programs, e.g., one or more circuits of computer program instructions, encoded on one or more computer storage media for execution by, or to control the operation of, data processing apparatus. Alternatively or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate components or media (e.g., multiple CDs, disks, or other storage devices).

The operations described in this specification can be performed by a data processing apparatus on data stored on one or more computer-readable storage devices or received from other sources. The term "data processing apparatus" or "computing device" encompasses various apparatuses, devices, and machines for processing data, including by way of example a programmable processor, a computer, a system on a chip, or multiple ones, or combinations of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a circuit, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more circuits, subprograms, or portions of code). A computer program can be deployed to be executed on one computer or on multiple computers that are located at one site or distributed across multiple sites and interconnected by a communication network.

Processors suitable for the execution of a computer program include, by way of example, microprocessors, and any one or more processors of a digital computer. A processor can receive instructions and data from a read only memory or a random access memory or both. The elements of a computer are a processor for performing actions in accordance with instructions and one or more memory devices for storing instructions and data. A computer can include, or be operatively coupled to receive data from or transfer data to, or both, one or more mass storage devices for storing data, e.g., magnetic, magneto optical disks, or optical disks. A computer need not have such devices. Moreover, a computer can be embedded in another device, e.g., a personal digital assistant (PDA), a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The implementations described herein can be implemented in any of numerous ways including, for example, using hardware, software or a combination thereof. When implemented in software, the software code can be executed on any suitable processor or collection of processors, whether provided in a single computer or distributed among multiple computers.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

A computer employed to implement at least a portion of the functionality described herein may comprise a memory, one or more processing units (also referred to herein simply as "processors"), one or more communication interfaces, one or more display units, and one or more user input devices. The memory may comprise any computer-readable media, and may store computer instructions (also referred to herein as "processor-executable instructions") for implementing the various functionalities described herein. The processing unit(s) may be used to execute the instructions. The communication interface(s) may be coupled to a wired or wireless network, bus, or other communication means and may therefore allow the computer to transmit communications to or receive communications from other devices. The display unit(s) may be provided, for example, to allow a user to view various information in connection with execution of the instructions. The user input device(s) may be provided, for example, to allow the user to make manual adjustments, make selections, enter data or various other information, or interact in any of a variety of manners with the processor during execution of the instructions.

The various methods or processes outlined herein may be coded as software that is executable on one or more processors that employ any one of a variety of operating systems or platforms. Additionally, such software may be written using any of a number of suitable programming languages or programming or scripting tools, and also may be compiled as executable machine language code or intermediate code that is executed on a framework or virtual machine.

In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the solution discussed above. The computer readable medium or media can be transportable, such that the program or programs stored thereon can be loaded onto one or more different computers or other processors to implement various aspects of the present solution as discussed above.

The terms "program" or "software" are used herein to refer to any type of computer code or set of computer-executable instructions that can be employed to program a computer or other processor to implement various aspects of embodiments as discussed above. One or more computer programs that when executed perform methods of the present solution need not reside on a single computer or processor, but may be distributed in a modular fashion amongst a number of different computers or processors to implement various aspects of the present solution.

Computer-executable instructions may be in many forms, such as program modules, executed by one or more computers or other devices. Program modules can include routines, programs, objects, components, data structures, or other components that perform particular tasks or implement particular abstract data types. The functionality of the program modules can be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Any references to implementations or elements or acts of the systems and methods herein referred to in the singular can include implementations including a plurality of these elements, and any references in plural to any implementation or element or act herein can include implementations including only a single element. References in the singular or plural form are not intended to limit the presently disclosed systems or methods, their components, acts, or elements to single or plural configurations. References to any act or element being based on any information, act or element may include implementations where the act or element is based at least in part on any information, act, or element.

Any implementation disclosed herein may be combined with any other implementation, and references to "an implementation," "some implementations," "an alternate implementation," "various implementations," "one implementation" or the like are not necessarily mutually exclusive and are intended to indicate that a particular feature, structure, or characteristic described in connection with the implementation may be included in at least one implementation. Such terms as used herein are not necessarily all referring to the same implementation. Any implementation may be combined with any other implementation, inclusively or exclusively, in any manner consistent with the aspects and implementations disclosed herein.

References to "or" may be construed as inclusive so that any terms described using "or" may indicate any of a single, more than one, and all of the described terms. References to at least one of a conjunctive list of terms may be construed as an inclusive OR to indicate any of a single, more than one, and all of the described terms. For example, a reference to "at least one of 'A' and 'B'" can include only 'A', only 'B', as well as both 'A' and 'B'. Elements other than 'A' and 'B' can also be included.

The systems and methods described herein may be embodied in other specific forms without departing from the characteristics thereof. The foregoing implementations are illustrative rather than limiting of the described systems and methods.

Where technical features in the drawings, detailed description or any claim are followed by reference signs, the reference signs have been included to increase the intelligibility of the drawings, detailed description, and claims. Accordingly, neither the reference signs nor their absence have any limiting effect on the scope of any claim elements.

The systems and methods described herein may be embodied in other specific forms without departing from the characteristics thereof. The foregoing implementations are illustrative rather than limiting of the described systems and methods. Scope of the systems and methods described herein is thus indicated by the appended claims, rather than the foregoing description, and changes that come within the meaning and range of equivalency of the claims are embraced therein.

What is claimed is:

1. An apparatus for a water resistant active exoskeleton boot, comprising:
   a shin pad to be coupled to a shin of a user and at least one housing of one or more housings;
   the one or more housings enclosing electronic circuitry and an electric motor that is configured to generate torque about an axis of rotation of an ankle joint of the user, wherein a sealant is placed in contact with the one or more housings to close the one or more housings and prevent an ingress of water into the one or more housings;

an output shaft coupled to the electric motor and extending through a bore in the one or more housings enclosing the electric motor;

a collar statically coupled with the output shaft;

a seal in contact with the collar and fixed to a portion of the one or more housings comprising the bore, the seal to prevent an ingress of the water into the one or more housings, the collar (1) disposed between the seal and the output shaft and (2) configured to rotate separately from the seal; and a rotary encoder enclosed within the one or more housings to measure an angle of the electric motor, wherein the electronic circuitry receives, from the rotary encoder, an indication of the angle of the electric motor and controls, based on the indication of the angle of the electric motor, operation of the electric motor configured to generate torque about the axis of rotation of the ankle joint of the user.

2. The apparatus of claim 1, wherein the seal comprises grease.

3. The apparatus of claim 1, wherein the seal comprises a gasket.

4. The apparatus of claim 1, wherein the sealant used to close the one or more housings comprises an adhesive sealant.

5. The apparatus of claim 1, wherein the sealant used to close the one or more housings comprises epoxy and permanently closes the one or more housings.

6. The apparatus of claim 1, comprising:
a battery pack configured to be coupled to the one or more housings below a knee of the user.

7. The apparatus of claim 1, wherein the one or more housings form a clamshell structure to enclose the electronic circuitry and the electric motor.

8. The apparatus of claim 1, comprising:
a second rotary encoder configured to measure an angle of the ankle joint, the second rotary encoder comprising a first component enclosed in the one or more housings and in communication with the electronic circuitry, and a second component located outside the one or more housings and configured to interact with the first component.

9. The apparatus of claim 8, wherein:
the first component of the second rotary encoder comprises a sensor,
the second component of the second rotary encoder comprises a magnetic component, and
the electronic circuitry configured to determine the angle of the ankle joint based on an interaction between the sensor and the magnetic component.

10. The apparatus of claim 9, comprising:
an aluminum housing separating the sensor from the magnetic component.

11. The apparatus of claim 9, wherein the sensor comprises a Hall effect sensor, and the magnetic component comprises a permanent magnet.

12. The apparatus of claim 1, wherein the rotary encoder comprises an inductive encoder.

13. The apparatus of claim 1, wherein at least one of the one or more housings is formed of plastic or aluminum.

14. A method of augmenting user motion, comprising:
providing, to a user, a water resistant active exoskeleton boot comprising:
a shin pad to be coupled to a shin of the user and at least one housing of one or more housings;
the one or more housings enclosing electronic circuitry and an electric motor that is configured to generate torque about an axis of rotation of an ankle joint of the user, wherein a sealant is placed in contact with the one or more housings to close the one or more housings and prevent an ingress of water into the one or more housings;

an output shaft coupled to the electric motor and extending through a bore in the one or more housings enclosing the electric motor;

a collar statically coupled with the output shaft;

a seal in contact with the collar and fixed to a portion of the one or more housings comprising the bore, the seal to prevent an ingress of the water into the one or more housings, the (1) collar disposed between the seal and the output shaft and (2) configured to rotate separately from the seal; and a rotary encoder enclosed within the one or more housings to measure an angle of the electric motor, the rotary encoder comprising a magnet disposed on a first side of the seal and an encoding sensor disposed on a second side of the seal opposite the first side of the seal, wherein the electronic circuitry receives, from the rotary encoder, an indication of the angle of the electric motor and controls, based on the indication of the angle of the electric motor, operation of the electric motor configured to generate torque about the axis of rotation of the ankle joint of the user.

15. The method of claim 14, wherein the seal in contact with the output shaft comprises grease.

16. The method of claim 14, wherein the sealant used to close the one or more housings comprises an adhesive sealant.

17. The method of claim 14, wherein the sealant used to close the one or more housings comprises epoxy and permanently closes the one or more housings.

18. The method of claim 14, comprising:
providing a battery pack coupled to the one or more housings below a knee of the user.

19. The method of claim 14, comprising:
providing a second rotary encoder to measure an angle of the ankle joint, the second rotary encoder comprising a first component enclosed in the one or more housings and in communication with the electronic circuitry, and a second component located outside the one or more housings and configured to interact with the first component.

20. An apparatus for a water resistant active exoskeleton boot, comprising:
a shin pad to be coupled to a shin of a user and at least one housing of one or more housings;
the one or more housings enclosing electronic circuitry and an electric motor that is configured to generate torque about an axis of rotation of an ankle joint of the user, wherein a sealant is placed in contact with the one or more housings to close the one or more housings and prevent an ingress of water into the one or more housings;

an output shaft coupled to the electric motor and extending through a bore in the one or more housings enclosing the electric motor;

a collar statically coupled with the output shaft;

a seal in contact with the collar and fixed to a portion of the one or more housings comprising the bore, the seal to prevent an ingress of the water into the one or more housings, the (1) collar disposed between the seal and the output shaft and (2) configured to rotate separately from the seal; and a rotary encoder enclosed within the one or more housings to measure an angle of the electric motor, the rotary encoder comprising a magnet disposed on a first side of the seal and an encoding sensor disposed on a second side of the seal opposite the first side of the seal,
wherein the electronic circuitry receives, from the rotary encoder, an indication of the angle of the electric motor and controls, based on the indication of the angle of the electric motor, operation of the electric motor configured to generate torque about the axis of rotation of the ankle joint of the user.

* * * * *